US012714871B2

(12) United States Patent
Schnell et al.

(10) Patent No.: US 12,714,871 B2
(45) Date of Patent: Aug. 25, 2026

(54) STIMULATION DEVICE AND USE THEREOF

(71) Applicant: STIMIT AG, Nidau (CH)

(72) Inventors: Pascal Schnell, Bärschwil (CH); Thomas Degen, Birmensdorf (CH); Dirk Fengels, Root (CH); Ronja Müller-Bruhn, Windisch (CH)

(73) Assignee: STIMIT AG, Nidau (CH)

( * ) Notice: Subject to any disclaimer, the term of this patent is extended or adjusted under 35 U.S.C. 154(b) by 988 days.

(21) Appl. No.: 17/769,122

(22) PCT Filed: Oct. 19, 2020

(86) PCT No.: PCT/EP2020/079406
§ 371 (c)(1),
(2) Date: Apr. 14, 2022

(87) PCT Pub. No.: WO2021/074455
PCT Pub. Date: Apr. 22, 2021

(65) Prior Publication Data

US 2024/0001132 A1 Jan. 4, 2024

(30) Foreign Application Priority Data

Oct. 18, 2019 (CH) .................................... 01327/19

(51) Int. Cl.
*A61N 1/40* (2006.01)
*A61N 1/04* (2006.01)
(Continued)

(52) U.S. Cl.
CPC ............... *A61N 1/40* (2013.01); *A61N 2/006* (2013.01); *A61N 2/02* (2013.01)

(58) Field of Classification Search
CPC . A61N 1/40; A61N 2/006; A61N 2/02; A61N 1/0456
See application file for complete search history.

(56) References Cited

U.S. PATENT DOCUMENTS 6,463,327 B1 10/2002 Lurie et al.
2006/0287566 A1 12/2006 Zangen et al.
(Continued)

FOREIGN PATENT DOCUMENTS

EP 3355987 A1 8/2018
GB 2587392 A 3/2021
(Continued)

OTHER PUBLICATIONS

International Search Report and Written Opinion issued Jan. 21, 2021 in Intl. Appl. No. PCT/EP2020/079406.

*Primary Examiner* — Carrie R Dorna
*Assistant Examiner* — Joshua Daryl D Lannu
(74) *Attorney, Agent, or Firm* — MEDLER FERRO WOODHOUSE & MILLS PLLC

(57) ABSTRACT

Disclosed are a stimulation device and method to coordinately stimulate two separate nerves in a human or animal body for activating a target tissue. The device includes a first coil unit configured to stimulate a first nerve, a second coil unit configured to stimulate a second nerve, and a bracket structure coupled to the first and second coil units. The bracket structure is adjustable such that positions and orientations of the first and second coil units relative to each other are adaptable to a target configuration wherein the first and second coil units are positioned whereby the first nerve is stimulable by the first coil unit and the second nerve is stimulable by the second coil unit. The bracket structure has a locking mechanism to block the position and orientation of the first and second coil units relative to each other in the target configuration.

20 Claims, 9 Drawing Sheets

(51) Int. Cl.
*A61N 2/00* (2006.01)
*A61N 2/02* (2006.01)

(56) References Cited

U.S. PATENT DOCUMENTS

| | | | | |
|---|---|---|---|---|
| 2011/0276112 | A1 | 11/2011 | Simon et al. | |
| 2014/0200388 | A1 * | 7/2014 | Schneider | A61N 2/006 600/15 |
| 2017/0291038 | A1 | 10/2017 | Midorikawa et al. | |
| 2022/0362570 | A1 | 11/2022 | Pemberton | |

FOREIGN PATENT DOCUMENTS

| | | | |
|---|---|---|---|
| WO | 0170332 | A2 | 9/2001 |
| WO | 2015/179744 | A1 | 11/2015 |
| WO | 2017/055471 | A1 | 4/2017 |
| WO | 2019/154839 | A1 | 8/2019 |
| WO | 2019/173866 | A1 | 9/2019 |
| WO | 2020/079266 | A1 | 4/2020 |
| WO | 2021059250 | A1 | 4/2021 |

* cited by examiner 95
93
933
932
94
942
941
931
9222
9122
926
916
928
918
915
925
917
927
924
921
911
914
92
922
91
928
918
9221
912
9121

93
95
933
9122
91
932
931
94
912
941
9222
916
928
925
918
911
927
928
92

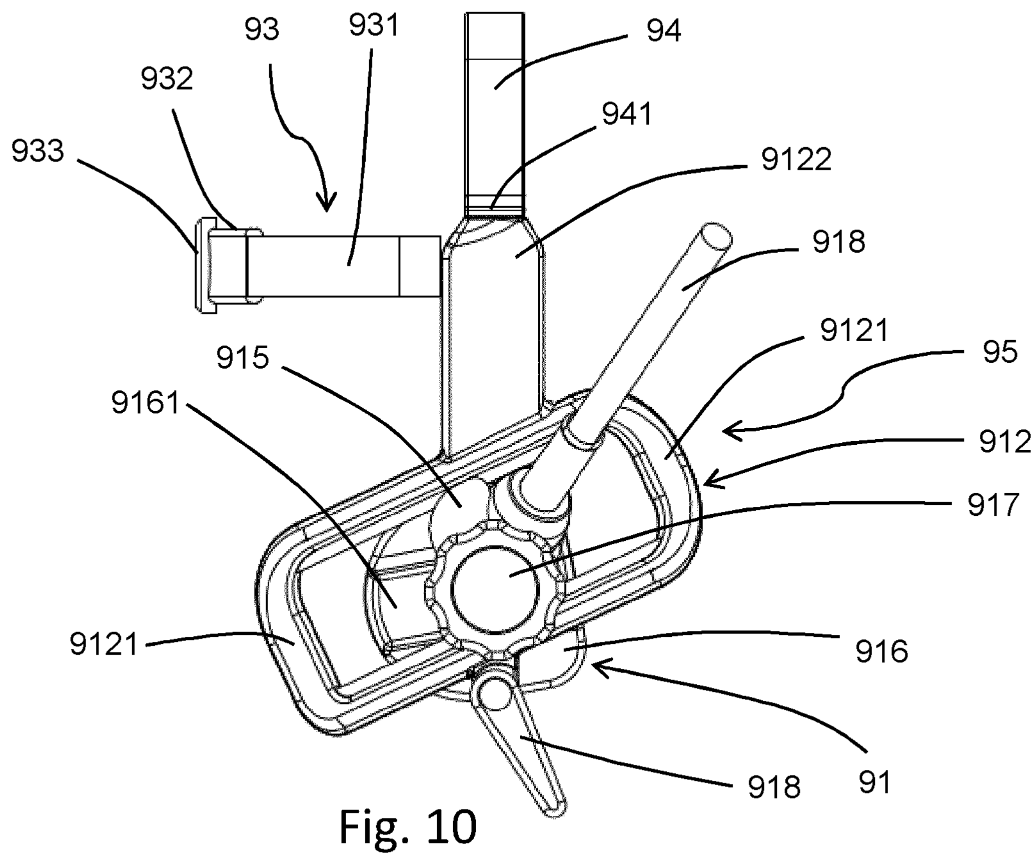
Fig. 10
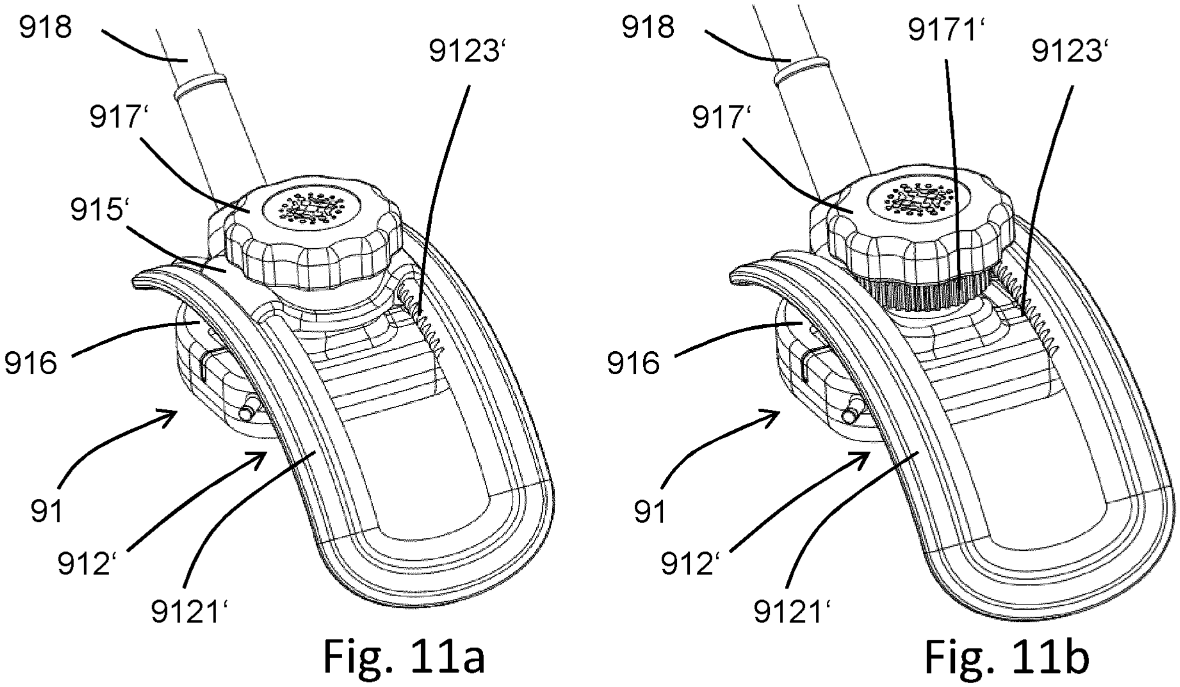
Fig. 11a
Fig. 11b

STIMULATION DEVICE AND USE THEREOF

TECHNICAL FIELD

The present invention relates to a stimulation device, and a method for stimulating two separate nerves in a human or animal body and thereby activating a target tissue. More particularly, the present invention relates to a non-invasive electro-magnetic stimulation device using a first coil winding unit for stimulating a first nerve and a second coil winding unit for stimulating a second nerve.

BACKGROUND ART

In medicine, it is known that for many purposes it is beneficial to activate a target tissue of a patient using stimulation by electro-magnetic fields. For achieving such activation of tissues in a patient's body, it is known to directly stimulate the tissue or to indirectly activate the tissue via stimulation of specific parts of the neural system. For example, the target tissue being a muscular tissue can be activated by providing electric pulses directly to the muscular tissue or to nerves associated to the muscular tissue.

In practice, electro-magnetic stimulators are used to activate a target tissue, which are based on the principle of electro-magnetic induction. A strong current pulse (typically a monophasic or biphasic current pulse) flows through a coil winding, which produces a strong, transient magnetic field. The current pulses cause a changing magnetic field that for example alters according to the phases of the current pulses. The changing magnetic field induces a corresponding electric field, which in turn depolarizes neuronal membranes, leading to action potentials through one or more nerves. Coil windings are usually designed towards generating electric field distribution curves of the induced field, often having an electric field peak (area with maximum electric field strength) or an electric field area, which is stronger than other fields in other areas. Thus, an electric field distribution curve can generate activation pulses, which are effective periodically at time intervals, and electric field peaks or strong field areas may alternate with low field areas in the distribution curve.

For example, US 2013/0131746 A1 discloses a non-invasive nerve stimulating device for stimulating a vagus nerve of a patient based on electro-magnetic stimulation. The device comprises a housing for accommodating a coil arrangement including two coils for generating an electro-magnetic field. The coils are located in head sections of the housing that are provided to be applied to a surface of a patient's body. The housing is held in place by straps or frames, or is held by hand. Both coils are positioned and oriented in the housing to stimulate the same nerve. To stimulate two separate nerves two separate of such stimulating devices would be required.

Another device for magnetic stimulation is shown in US 2017/0291038 A1. The device is used for stimulating intracerebral nerves by placing the device on the skull of a patient. The device includes two basically flat spiral conductive coils that are arranged in a casing such that the coils partially overlap and are targeted towards a nerve to be stimulated. The coils are positioned in the casing by molding. The casing comprises a coil bottom face and is curved to placed on the skull, wherein the casing is held in place by a standing rack. Again, for stimulating two separately located nerves two of such devices are needed.

In critical care units of hospitals it may be desired to activate the diaphragm of ventilated patients in order to prevent drawbacks of disuse of the diaphragm. It was shown that disuse atrophy of diaphragm muscle fibres occurs already in the first 18-69 hours of mechanical ventilation, and the muscle fibre cross-sections decreased by more than 50% in this time. Thus, it is aimed to activate the diaphragm repeatedly while the patient is given artificial or mechanical respiration such that the functioning of the diaphragm can be upheld, or to activate the diaphragm at least during the weaning period to support effective restoration of independent respiratory function.

It is known that the diaphragm can be activated by stimulating the two nerves, e.g., at the neck of a patient. In this context, US 2016/0310730 A1 describes an apparatus for reducing ventilation induced diaphragm disuse in a patient receiving ventilation support from a mechanical ventilator. The apparatus includes an electrode array of first and second types and comprises a plurality of electrodes configured to stimulate a nerve of the patient. The electrode arrays are configured as surface electrode arrays embedded in adhesive electrode patches to be placed on each side of a patient's neck near the areas where the nerves are located. Thus, the electrode arrays are electrically and mechanically coupled to the skin of the patient independent from each other. Therefore, the electrode arrays cover portions of a patient's surface and may interfere with other applications required for the treatment of the patient like for example the intubation into the trachea. In case the electrode arrays need to be taken off and replaced at a later point in time, the system needs to be fully re-calibrated according the new locations of the electrode arrays to avoid undesired co-stimulation of tissue surrounding the nerves.

When two target nerves inside the body in a close distance to each other shall be stimulated simultaneously, the coil winding systems in today's stimulators used for electro-magnetic stimulation have significant limitations. De-central coils have been designed for this purpose producing de-centralized fields and have been described for instance in DE 10 2007 013531 A1. However, typically two separate stimulator devices are necessary, the electromagnetic fields of the two devices can interfere with each other, and body constraints may not allow positioning coils windings of the two devices in parallel to make use of the de-centralized design. Especially in the neck region, positioning coil windings longitudinal to the neck would force the user to choose significantly smaller coil winding sizes because the chin and chest constrain space for the coils to be placed.

Therefore, there is a need for a non-invasive stimulation device and use thereof and a non-invasive method for stimulating two separate nerves in a human or animal body, which allow for efficient stimulation of the two nerves, overcome space constraints, avoid co-stimulation effects of tissue in the vicinity of the nerves, are simple to apply at a body as well as convenient and pain-free for the human or animal.

DISCLOSURE OF THE INVENTION

According to the invention this need is settled by a stimulation device as it is defined by the features of the first independent claim, and by a method for stimulating two separate nerves in a human or animal body as it is defined by the second independent claim. Preferred embodiments are subject of the dependent claims.

In particular, the invention provides a stimulation device to coordinately stimulate two separate nerves in a human or animal body for activating a target tissue in the human or animal body. The stimulation device comprises a first coil unit configured to be positioned at the human or animal body to stimulate a first nerve of the two separate nerves, a second coil unit configured to be positioned at the human or animal body to stimulate a second nerve of the two separate nerves, and a bracket structure coupled to the first coil unit and the second coil unit. The bracket structure is adjustable such that positions and orientations of the first coil unit and of the second coil unit relative to each other are adaptable to a target configuration of the bracket structure in which the first coil unit and the second coil unit are distinctly positioned at the human or animal body such that the first nerve can be stimulated by the first coil unit and the second nerve can be stimulated by the second coil unit. Further, the bracket structure has a locking mechanism to block the position and orientation of the first coil unit and the second coil unit relative to each other in the target configuration.

The bracket structure may be provided with at least one articulation, preferably with several articulations, for adjusting the positions and orientations of the first and second coil units. Such articulations may for example be realized as mechanical hinges, rotation joints, ball bearing and the like. According to the invention, the locking mechanism is configured to block each of the articulations of the bracket structure to freeze the coil units relative to each other in their target configuration.

The term, "positioned at" as used herein can relate to being located at the body by contacting it. For example, the first and second coil unit can be positioned at the body by lying on it. When being positioned at the body, the first and second coil units can form support points and determine defined contact points on the body. Like this, the stimulation device can be precisely positioned with respect to the two nerves. Further, by choosing a specific target configuration of the bracket structure and specific contact points on the body a defined location of the stimulation device with respect to the body may be determined.

In an advantageous embodiment of the stimulation device, the bracket structure comprises one or more vacuum elements configured to attach the stimulation device to the human or animal body. The vacuum elements can be realized as suction cups or the like. The vacuum elements facilitate positioning and releasably fastening the coil units to the body after the target configuration of the bracket structure is adjusted and locked in place.

The stimulation device according to the invention can easily be adjusted to specific individual characteristics of a body or for coordination with other medical devices for treatment of the human or animal. At the same time the electro-magnetic field generated for stimulating the nerves can be optimized for activating a target tissue and for avoiding co-stimulation of other tissues. By blocking the position and orientation of the first and second coil unit accidental or unintentional misalignment of the coil unit relative to the body can be avoided rendering the use of the stimulation device safe and efficient. Also, the device can efficiently be re-positioned at the body after being temporarily removed therefrom.

The method of stimulating two separate nerves in a human or animal body for activating a target tissue in the human or animal body according to the invention uses such a stimulation device. The method comprises adjusting the bracket structure of the stimulation device such that positions and orientations of the first coil unit of the stimulation device and of the second coil unit of the stimulation device relative to each other are adapted to a target configuration in which the first coil unit and the second coil unit are distinctly positioned at the human or animal body such that a first nerve of the patient can be stimulated by the first coil unit and a second nerve of the patient can be stimulated by the second coil unit. Further, the method comprises locking the bracket structure to block the position and orientation of the first coil unit and the second coil unit relative to each other in the target configuration.

The stimulation device can particularly be a stimulation device to coordinately stimulate two Phrenic nerves of a patient for activating a diaphragm of the patient. For example, the stimulation device can be embodied as a respiration promoting apparatus. In this case, the stimulation device may be adjusted for being applied to the patient's neck to generate a localized electro-magnetic field in a localized gap between the larynx and the sternocleidomastoid muscle. Thus, the Phrenic nerves at a depth of about 2-4 cm inside a patient's neck can be stimulated through the available gap between the larynx and the sternocleidomastoid muscle by generating a coordinated electro-magnetic field in the first and second coil unit. Advantageously, the electro-magnetic field does not extend field amplitudes over a certain threshold level. Thus, the electro-magnetic field does not extend too far beyond the target area of the Phrenic nerves and therefore does not affect or co-stimulate the larynx and the sternocleidomastoid muscle.

In an advantageous embodiment of the stimulation device the locking mechanism of the bracket structure is configured to irreversibly block the position and orientation of the first coil unit and the second coil unit relative to each other in the target configuration. Like this, a distance between the first and second coil units and the orientation of the coil units towards each other, e.g. tilting angle, are permanently fixed. Using a reference contact point on a patient's body, will automatically place the first coil unit and the second coil unit at the desired contact points for the coil units and for production of the electro-magnetic fields.

Further, the first coil unit and the second coil unit can be detachably coupled to the bracket structure. In this case, the bracket structure can easily be replaced in case needed, or the coil units can be exchanged if necessary. Also, the bracket structure can be designed as a disposable such that for example the bracket structure be discarded after use for one patient. Thus, a possible cross contamination when using the stimulation device for different patients can be prevented and the application of the stimulation device can be simplified. The material selected for the bracket structure can be of lesser quality than required for a reusable bracket structure, since, e.g., it does not have to be sterilizable.

In an embodiment of the stimulation device according to the invention, the bracket structure is configured to adjust a distance between the first coil unit and the second coil unit to a target distance of the target configuration. Thus, the positioning of the first and second coil unit relative to the body can be optimized with respect to the location of the two nerves in the body. Advantageously, the locking mechanism is configured such that the bracket structure can mechanically prevent any further adjustment of the distance between the first coil unit and the second coil unit once the distance is set to a target configuration.

Preferably, the bracket structure comprises a first leg portion, a second leg portion and a hinge portion connecting the first leg portion and the second leg portion to each other. The leg portions can be realized for example by an elongated stiff element, like a bar or a rod. The hinge portion can be realized as any articulated joint that connects the first and second leg portions in an articulated manner, for example a swivel joint or a ball joint. The first coil unit is coupled to the first leg portion and the second coil unit is coupled to the second leg portion. For example, the first and second coil units are coupled to one end of a first and second leg element, respectively, and the hinge portion is arranged at an opposing end of these elements and flexibly couples the first and second leg elements. A distance between the first coil unit and the second coil unit can be adjusted by pivoting the first leg portion and the second leg portion relative to each other about the hinge portion. Thus, the bracket structure configuration can easily be adjusted by selecting a pivoting position of the first leg portion relative to the second leg portion, and the position and orientation of the first and second coil units can be adapted for applying the stimulation device at a defined location of a patient.

For such a bracket structure the locking mechanism is configured to mechanically prevent the hinge portion from pivoting the first leg portion and the second leg portion relative to each other. Thus, the adjusted bracket structure configuration is fixed and reliable and stable positioning of the stimulation device is provided.

Preferably, the bracket structure is configured to adjust a first orientation of the first coil unit to a first target orientation of the target configuration and a second orientation of the second coil unit to a second target orientation of the target configuration. like this, direction and distribution of an electro-magnetic field generated by the stimulation device can be adapted to the stimulation requirements of the two nerves. Particularly, an angle between a first winding axis of the first coil unit and a second winding axis of the second coil unit can be adapted as well as the angle of the winding axes relative to the nerves. Advantageously, the blocking mechanism is configured to mechanically prevent adjustment of the first orientation and of the second orientation of the coil units. Thus, the target orientation configuration of the bracket structure can be blocked in optimized position for stimulating the nerves. Preferably, the bracket structure is designed for mechanically blocking the target orientation configuration. Thus, a blocking of first and second coil units can be released by disconnecting the coil units from the bracket structure. Alternatively, the locking mechanism could be provided by applying a chemical component on the bracket structure for fixation of the bracket structure after adjustment of a distance and an orientation of the coil units. The chemical component could for example be provided by a foam that is hardening after application on or into the bracket structure adjacent to the adjustable components of the bracket structure. Openings could be provided to in the bracket structure to provide access to articulation areas of the bracket structure.

Preferably, the bracket structure comprises a first pivoting coupler and a second pivoting coupler. The first coil unit is mounted to the first pivoting coupler and the second coil unit is mounted to the second pivoting coupler. For example, the first pivoting coupler can extend from a first leg portion and the second pivoting coupler can extend from a second leg portion, wherein the first and second leg portions may for example be realized as mentioned above.

The first and second pivoting couplers can be identical. They can be realized with an articulation bearing that couples the first and second coil units in a moveable manner to the bracket structure or the first and second leg portion, respectively. Advantageously, a pivoting coupler includes more than one articulation axis such that a coil unit can be moved relative to the bracket structure in more than one direction. Preferably, the first pivoting coupler is configured to provide pivoting the first coil unit relative to the bracket structure about two essentially perpendicular axes and the second pivoting coupler is configured to provide pivoting the second coil unit relative to the bracket unit about two essentially perpendicular axes.

The pivoting couplers allow for adjustment of the orientation of the first coil unit and the second coil unit relative to each other and relative to the patient without moving other parts of the bracket structure as for example the first and second leg portions relative to each other. Thus, the pivoting couplers provide a fine-tuning option for aligning an electro-magnetic field generated by the coil units with respect to their assigned nerves while other body tissues are avoided by the field.

For example, the first pivoting coupler is pivotably mounted to the first leg portion such that the first pivoting coupler can be pivoted relative to the first leg portion about an articulation axis defined by the first leg portion, and respectively the second pivoting coupler is pivotably mounted to the second leg portion such that the second pivoting coupler can be pivoted relative to the second leg portion about an articulation axis defined by the second leg portion. The articulation axis can for example be arranged along a longitudinal axis of the leg portions. The pivoting coupler and the coil unit as a whole can be moved relative to their leg portion. For example, the pivoting coupler is located basically on the articulation axis of the leg portion and is rotated about that axis relative to the leg portion. Thus, the coil unit basically remains in position towards the bracket structure and the patient, respectively, but changes its angle adjustment and therefore the direction of generating the electro-magnetic field.

Additionally or alternatively, the first coil unit can be pivotably mounted to the first pivoting coupler such that the first coil unit may be pivoted relative to the first pivoting coupler about an articulation axis of the first pivoting coupler, and the second coil unit can be pivotably mounted to the second pivoting coupler such that the second coil unit may be pivoted relative to the second pivoting coupler about an articulation axis of the second pivoting coupler. Accordingly, the orientation of the coil units relative to their respective pivoting coupler can be adapted. For example, the coil unit is located basically on the pivoting coupler articulation axis and is rotated about that axis relative to the pivoting coupler. Therefore, the direction of areas where electro-magnetic fields are generated by the first and second coil units of the stimulation device can be changed without adjusting the position of the coil units relative to the patient and without adjusting the first and second leg portion relative to each other simply by adjusting the orientation of the coil units. Again, the adjustable nature of the coil units of the stimulation device facilitates optimal stimulation of the nerves and simplifies positioning of the device at a patient.

Advantageously, the articulation axis along the first leg is essentially perpendicular to the articulation axis of the first pivoting coupler and the articulation axis along the second leg is essentially perpendicular to the articulation axis of the second pivoting coupler. Consequently, the first and the second coil units are supported by the pivoting couplers such that the areas of the first and second electro-magnetic fields generated by the coil units can be adapted to any desired direction relative to the stimulation device. Therefore, the coil units can be small and overcome space constrains, a targeted alignment of the electro-magnetic fields can avoid co-stimulation effects of tissue in the vicinity of the nerves and the low-weight structure of the stimulation device allows for convenient positioning at the patient.

Advantageously, the blocking mechanism may be configured to mechanically prevent the first pivoting coupler from pivoting the first coil unit and the second pivoting coupler from pivoting the second coil unit. For example, pivoting shafts corresponding to the articulation axes may be mechanically blocked.

In case the first coil unit and the second coil unit are detachably coupled to the bracket structure, the coil units may be releasable from the pivoting coupler. Alternatively or additionally, the pivoting coupler may be detachably coupled to the leg portion of the bracket structure. Thus, the coil units may be used with differing types of bracket structure or with differing types of pivoting couplers. Also, the bracket structure or the pivoting couplers can easily be replaced or discarded without the need for new coil units, which the more complex and costly components of the stimulation device. Detachable coil units help to safe costs for a patient's treatment and allow for the customization of the stimulation device with respect to a patients needs.

In summary, the locking mechanism is provided to block the position and orientation of the first coil unit and the second coil unit relative to each other in a target configuration of the stimulation device and the bracket structure, respectively. That means the locking mechanism locks a movement of the leg portions at the hinge portion, a movement of the pivoting coupler relative to the leg portions and a movement of the coil units relative to the pivoting coupler. In general, the locking mechanism can be any suitable mechanism for stopping such movements and keeping the bracket structure in the target configuration after adjustment. Preferably, the locking mechanism is realized as a mechanical locking structure. However, also an electrical locking arrangement could be used.

A mechanical locking mechanism is for example realized by a form fit between parts of the bracket structure to be blocked or between a part of the bracket structure and an additional blocking part. A form fit can for example be established within the hinge portion. A blocking part, like a locking button, may be arranged at the hinge portion to be a pushed in or turned to block movements provided by the hinge portion. Similar, a form fit could be provided for the pivoting coupler. Alternatively or additionally, the mechanical locking mechanism could block the bracket structure by frictional locking. Also, a combination of form fit and friction could be used to block the bracket structure. The locking mechanism can prevent changes of the configuration of the bracket structure after the target configuration has been adjusted, which guarantees adequate stimulation of the nerves by the stimulation device. Thus, for example the stimulation device can be removed from the patient and replaced at a later point in time without the need of recalibration of the coil units.

In another preferred embodiment of the stimulation device of the invention, the bracket structure comprises a first frame portion, a second frame portion and a forehead support structure. Thereby, the first coil unit is coupled to the first frame portion and the second coil unit is coupled to the second frame portion, the first frame portion and the second frame portion are connected via the forehead support structure, and the forehead support structure is configured to be positioned at and to contact a forehead of the patient. The forehead support structure can establish or include the third forward face.

Such a bracket structure allows for safely and conveniently mount the stimulation device to the patient and to securely supporting or holding the stimulation device at an appropriate location or position. In particular, it can be achieved that the coil units are stably located at the patient. Further, such bracket structure may allow for sophisticatedly adjusting the exact position and orientation of the coil units such that the Phrenic nerves can efficiently be stimulated. Also, such bracket structure allows for keeping a front side of the patient and, in particular, a front side of his neck and torso free and accessible. Like this, parallel treatment of the patient and treatment comfort can be enhanced.

The forehead support may be embodied in a cap- or hut-like manner to be worn by the patient such that the frame portions are correctly positioned and such that the forehead of the patient support the stimulation device. Preferably, the bracket structure comprises an overhead arch having a first tangential end and a second tangential end, the first frame portion is mounted to the first tangential end of the overhead arch, and the second frame portion is mounted to the second tangential end of the overhead arch. Like this, the stimulation device may be designed similar to a headphone additionally having the forehead support. Such configuration allows for an efficiently applicable safe mounting and operation of the stimulation device.

Thereby, the bracket structure is configured such that a distance between the overhead arch and the first coil unit and a distance between the overhead arch and the second coil unit are adjustable. In particular, the overhead arch or the first and second frame portions may be height adjustable. Like this, the first and second coil units can be properly positioned at the neck of the patient for stimulating the Phrenic nerves. Such distance adjustable bracket structure may form part of the locking structure as it allows to customize the device to an individual patient.

The forehead support structure of the bracket structure preferably is configured to be adjusted in accordance with a size of the forehead of the patient. Such adjustable forehead support can form part of the locking mechanism allowing for accurately sizing the device to an individual patient.

Preferably, the forehead support structure of the bracket structure comprises a band configured to extend along the forehead of the patient. Such band allows for a safe and easily adjustable implementation of the forehead support.

The forehead support structure of the bracket structure further preferably comprises a pad configured to contact the forehead of the patient. Such pad, which can be the third forward face, allows for providing a convenient and safe support on the forehead of the patient.

Preferably, each of the first frame portion and the second frame portion comprises a neck position guide section to which the first coil unit and the second coil unit, respectively, is movably mounted such that the first coil unit and the second coil unit can be varyingly positioned about a neck of the patient. For example, the neck position guide section may be embodied in a rail like fashion, wherein the coil units are configured to be held such that they can be slid or moved along the neck position guide. Advantageously, the neck position guide is bent such that it may more or less follow the neck when being positioned aside the neck of the patient.

Preferably, the locking mechanism of the bracket structure comprises a first fastening member coupled to the first coil unit and configured to be in a fixed state, in which the first coil unit is immovably fastened, and in a loose state, in which the first coil unit is movable, and a second fastening member coupled to the second coil unit and configured to be in a fixed state, in which the second coil unit is immovably fastened, and in a loose state, in which the second coil unit is movable. Such first and second fastening members allow for efficiently fix or release the first and second coil units as desired. Like this, it can be achieved that the device is locked in a configuration specifically suitable for an individual patient.

Thereby, the first coil unit preferably is mounted to the neck position guide section of the first frame portion by the first fastening member of the locking mechanism, wherein in the fixed state the first coil unit is immovably fastened to the neck position guide section of the first frame portion and in the loose state the first coil unit is movable relative to the neck position guide section of the first frame portion, and the second coil unit preferably is mounted to the neck position guide section of the second frame portion by the second fastening member of the locking mechanism, wherein in the fixed state the second coil unit is immovably fastened to the neck position guide section of the second frame portion and in the loose state the second coil unit is movable relative to the neck position guide section of the second frame portion.

Preferably, the first coil unit is mounted to the neck position guide section of the first frame portion by a first fastening member configured to be in a fixed state, in which the first coil unit is immovably fastened to the neck position guide section of the first frame portion, and in a loose state, which the first coil unit is movable relative to the neck position guide section of the first frame portion, and the second coil unit is mounted to the neck position guide section of the second frame portion by a second fastening member configured to be in a fixed state, in which the second coil unit is immovably fastened to the neck position guide section of the second frame portion, and in a loose state, which the second coil unit is movable relative to the neck position guide section of the second frame portion. By means of the first and second fastening members the position and orientation of the first coil and second units relative to each other can be blocked in a target configuration. Thus, such first and second fastening members may establish a locking mechanism allowing to preserve a configuration set to the individual situation given at a specific patient.

Each of the first and second fasting members can be embodied by a screw and a corresponding counterpart such as a guide element set in the respective neck position guide section. Alternatively, each of the first and second fasting members comprise a toothing and a screw with a cogwheel snapping in at varying distinct positions in the toothing.

Preferably, the bracket structure comprises two support structures configured to support the stimulation device on a torso of the patient. By such support structures the stimulation device may be particularly securely be supported on the patient's body. It may be achieved that the stimulation device contacts the body at three comparably solid portions of the body such as the forehead and the two clavicles of the patient.

Thereby, one of the two support structures preferably is comprised by the first frame portion and the other of the two support structures is comprised by the second frame portion. Like this, the frame portions themselves may be supported at the patient's body such as at his clavicles or the like.

Alternatively or additionally, one of the two support structures preferably comprises a first support bar movably connected to the first frame portion and the other of the two support structures preferably comprises a second support bar movably connected to the second frame portion. The support bars can be movable by being pivoted relative to the respective frame portion. Like this, a torso support can be provided which can be adjusted to the given situation of the specific patient. Also, such configuration allows to efficiently support the stimulation device at various portions of the torso such as at the clavicles, ribs or sternum.

In a further embodiment, the stimulation device according to the invention may comprise a reference structure configured to repeatedly locate the stimulation device at a target position of the human or animal body. The reference structure can be designed as a member allowing to connect the stimulation device at a specific portion of the body and a defined location such as at a landmark thereof. By having the reference structure, e.g. using the natural landmarks of the body, the stimulation device can conveniently be re-positioned at the body such that it can be assured that the first and second coil units are properly positioned and oriented to stimulate the first and second nerves.

In one example embodiment, the reference structure comprises at least two through-holes provided in the bracket structure and designed to allow providing markers to the human or animal body there through. The markers can, for example, be provided by a pen or something similar applying a visual sign on the human or animal body. The through-holes can for example be provided at leg portions of the bracket structure as described before. Also, a through-hole can be provided at the hinge portion of the bracket structure.

In another example embodiment, the reference structure comprises at least two connector members configured to be connected to respective connector members applied to the human or animal body. Thus, the stimulation device can be precisely adjusted to a target configuration required to connect the connector member arranged at the stimulation device to the connector members arranged at the body. The bracket structure can be blocked in this target configuration to conveniently establish connection between the connector member pairs.

Preferably, the stimulation device according to the invention the first coil unit has a first forward face configured to be positioned at the human or animal body, the second coil unit has a second forward face configured to be positioned at the human or animal body, and the bracket structure has a third forward face configured to be positioned at the human or animal body. The stimulation device is configured to be arranged at a defined location of the patient by the first forward face, the second forward face and the third forward face being positioned at the patient. The first and second forward faces of the first and second coil unit can for example be arranged on a housing of the coil units. Further, the forward faces can correspond to a specific side of a coil winding arranged in the housing.

Preferably, the third forward face is located at the hinge portion of the bracket structure. Thus, when the stimulation device is positioned at the patient and the third forward face lies on the patient, the hinge portion can serve as a reference support point for aligning the first and the second coil unit relative to the patient. Also, the hinge portion can serve as a symmetry axis or plane, which facilitates coordinated adaption of the position and orientation of the coil units by analogue alignment of the first and second leg portion. Thus, a customized positioning of the stimulation device on the patient's body is possible.

Further, the stimulation device may comprise a control unit configured to coordinatedly provide current to the first coil unit and to the second coil unit, respectively. Advantageously, the control unit is configured to simultaneously provide current to the first coil unit and to the second coil unit. Thus, by coordinating each of the current flows in the first and second coil unit the stimulation device can coordinatedly stimulate the two nerves as required for optimal activation of the target tissue.

Also, the control unit can comprise a power supply coupled to a first coil winding in the first coil unit and to a second coil winding in the second coil unit. Preferably, the control unit is configured such that the power supply provides current through the first coil winding in a circulation direction and through the second coil winding in the same circulation direction. The term "circulation direction" can particularly relate to a clockwise or counter clockwise direction. In such an embodiment, the first and second coil units may be operated in a reverse current mode. Like this, the electromagnetic fields generated by the two coil units can cancel each other in an area between the coil units. Thereby, undesired effects or side effects affecting the patient can be prevented. Also, it can be prevented that the coil units disturb each other in operation.

Thus, the control unit may comprise an electro-magnetic field adjustment mechanism that is configured to automatically adjust or vary a field strength or amplitude of the electro-magnetic field generated by the first and second coil units of the stimulation device. Particularly, when a predefined threshold of the electro-magnetic field is reached, the field will be reduced and adjusted. Also, the electro-magnetic field adjustment mechanism may automatically stop variation of the field strength of the electro-magnetic field when a satisfying activation feedback is received for example from the biofeedback sensors arranged at the coil unit. Thus, the control unit allows to efficiently adjust and dimension the electro-magnetic field or its required shape in order to achieve desired depolarization of the membrane of the nerves without negative effects on surrounding tissue.

The control unit also may signal the satisfying nerve activation feedback as an indicator that the chosen bracket structure configuration equals an optimal configuration and can serve as a target configuration. Therefore, in case the stimulation device needs to be re-adjusted—for example after taking of the apparatus for other treatments of the patient—the target configuration can easily reproduced.

Furthermore, in case that the locking mechanism is realized as an electrical locking mechanism, the control can provide a locking signal to switches of the electrical locking mechanism for blocking the configuration of the bracket structure when the target configuration is reached.

In a further embodiment of the stimulation device of the invention the first coil unit has a non-flat first coil winding formed from a conductive elongate component, and the second coil unit has a non-flat second coil winding formed from a conductive elongate component. The conductive elongate component is for example a copper or aluminium wire as commonly used for electric coils. However, other electrically conductive materials may be used as well. The first coil winding and the second coil winding can be formed of individual conductive elongate component.

Thereby, in one advantageous variant at least one of the first coil winding and the second coil winding is a convex coil winding. For example, such convex coil winding may result from several spiral-like turns which together form an outwards curved exterior surface of the coil windings. Therefore, the first and the second coil winding can have a convex outer side and a concave inner side. Particularly, the first coil winding and the second coil winding may have an essentially conical shape. Like this, the coil windings can be cone coils or cone coil windings. Also, at least one of the convex coil windings may have a cross section along a winding axis in an essentially parabolic shape, i.e. the parabolic shape can form a portion of a parabola. Further, at least one of the convex coil windings may have a cross section in an essentially spherical shape, which means each of the convex coil windings may have a cross section in an essentially spherical shape. Thereby, the spherical shape can form a portion of a circle.

The outwards curved exterior surface of the coils can be positioned on soft body tissue and with slight, physiologically tolerable pressure on the coils (e.g. created by the coil weight itself). Thus, the coil windings on the outwards curved exterior surface that is impressed into the body can get closer to the target nerve. Any distance reduction between coil wire and target nerve will result into higher effectiveness because electro-magnetic fields are reduced exponentially with increasing distance to the source.

Alternatively, in another advantageous variant at least one of the first coil winding and the second coil winding is designed as essentially cylindrical coil winding. Thus, the coil windings may have a cross section in an essentially cylindrical shape. In this case the rim or edge of an outermost winding can be positioned on the skin and may be pressed to the body just as mentioned for convex shaped coil windings.

Advantageously, both coil windings have the same non-flat shape. Thus, for example each of the coil windings has a cross section in an essentially parabolic shape, in an essentially conical shape or an essentially cylindrical shape.

Furthermore, each or at least one of the first non-flat coil winding and the second non-flat coil winding may have an oval base shape. The base shape can for example be defined by the outermost turn or winding of the coil windings. Generally, all of the spiral-like turns of the coil winding may have an oval shape similar to the oval base shape. However, due to the non-flat nature of the first and second coil winding, turns with a small radius that are close to the coil winding axis may have a shape differing from the turns with larger radii further away from the coil winding axis. The oval base shape may comprise an elliptic shape or a parabolic shape at opposing sides of the winding. By providing coil windings with oval base shapes, oval electro-magnetic fields can be generated. Like this, the electro-magnetic fields can be longitudinally stretched such that, under certain circumstances, the electro-magnetic field can be better provided distant from muscular structures towards the Phrenic nerves. For example, the longitudinally extending electro-magnetic fields facilitate the positioning of the coil units near or adjacent to the sternocleidomastoid muscles for stimulating the Phrenic nerves. Like this, side effects in use of the stimulation device can be lowered or prevented. In case the first and second coil windings are cylindrical, an oval base shape may allow for providing a comparably large contact surface by locating a wide curved portion of the oval base shape at the patient such that the coil units can be safely and stably positioned at the patient. Or, the oval base shape may allow to apply a comparably narrow electro-magnetic field to the patient by positioning the narrow curved portion of the oval shape at the patient and/or to impress the coil unit to a comparably large extent into the skin of a patient. In general, by designing the coil windings with the oval base shape, the electro-magnetic field can be geometrically shaped as desired.

Advantageously, each of the first and second coil units is bent or curved. More specifically, the forward faces of the first and second coil units can be bent or curved. Like this, the coil units can be designed to extend about or adjacent to a neck of the patient. Particularly, the radius of the curve can be in a range of a human or animal neck.

In a preferred embodiment, the method according to the invention comprises a step of obtaining an activation biofeedback indicative for the activation of the target tissue induced by the stimulation of the two nerves, wherein adjusting the bracket structure comprises varying the positions and orientations of the first and second coil units of the stimulation device and stopping variation of the first and second coil units of the stimulation device when the activation biofeedback is satisfying. Such method involving the biofeedback allows for efficiently setting up the stimulation in a particularly suitable and efficient manner. More specifically, such method allows efficiently re-finding or re-arranging an individual position and orientation of the coil units such that they can easily be reused in a subsequent therapy without requiring multiply setting and evaluation the best or appropriate position and orientation.

The term "biofeedback" as used herein can relate to any type of biological feedback. For example, the biofeedback may be a contraction or other movement of the target tissue induced by activating the target tissue.

Preferably, the method further comprising a step of arranging a biofeedback sensor to sense for an activation of the target tissue, wherein the activation biofeedback is obtained by provision of a sensor signal generated by the biofeedback sensor. The biofeedback sensor can be the sensor of the stimulation device mentioned above or any other sensor involved.

Preferably, when varying the positions and orientations of the first and second coil units of the stimulation device the activation biofeedback is gathered, the gathered activation biofeedbacks of the varied positions and orientations of the first and second coil units of the stimulation device are compared to each other and the position and orientation of the first and second coil units of the stimulation device having the best activation biofeedback is selected as the position and orientation of the first and second coil units of the stimulation device with the satisfying activation biofeedback. Such evaluation and setting of the position and orientation of the coil units allows for locking and reusing the coil units in a particular appropriate and efficient manner.

BRIEF DESCRIPTION OF THE DRAWINGS

The stimulation device and the method for promoting respiration of a patient according to the invention are described in more detail herein below by way of exemplary embodiments and with reference to the attached drawings, in which:

FIG. 10 shows a front view of the respiration promoting apparatus of FIG. 8;

FIG. 11*a* shows a portion of a seventh embodiment of respiration promoting apparatus according the invention; and FIG. 11*b* shows the portion of FIG. 11*a*, wherein a guide member is removed.

DESCRIPTION OF EMBODIMENTS

FIGS. 1 to 5 show different embodiments of stimulation devices according the present invention, which comprise a bracket structure coupled to coil units of the device for positioning and orienting the coil units relative to each other and stimulating two nerves. FIGS. 6 and 7 schematically show the concepts and applications of a stimulation device of the invention for coordinatedly stimulating the two nerves, particularly for stimulating the two Phrenic nerves of a human being. Further, a method of using a stimulation device according to the present invention may use any of the stimulation devices and concepts disclosed in FIGS. 1 to 7. Particularities of the method will be become apparent in context with the illustrated example embodiments. The example embodiments of a stimulation device shown in FIGS. 1 to 5 may take advantage of the concepts and applications as disclosed in FIGS. 6 and 7, but also may use other, more conventional coil arrangements.

In the following description certain terms are used for reasons of convenience and are not intended to limit the invention. The terms "right", "left", "forward", "backward", etc. refer to positions relative to a patient unless otherwise indicated the description. The terminology comprises the explicitly mentioned terms as well as their derivations and terms with a similar meaning. Also, spatially relative terms, such as "beneath", "below", "larger", "above", "upper", "smaller", "proximal", "distal", and the like, may be used to describe one element's or feature's relationship to another element or feature as illustrated in the figures or indicated in the description.

To avoid repetition in the figures and the descriptions of the various aspects and illustrative embodiments, it should be understood that many features are common to many aspects and embodiments. Omission of an aspect from a description or figure does not imply that the aspect is missing in embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part or component are provided with reference signs it is referred to other drawings showing the same part or component. Like numbers in two or more figures represent the same or similar elements or elements with the same functionality.

Figure 1A:
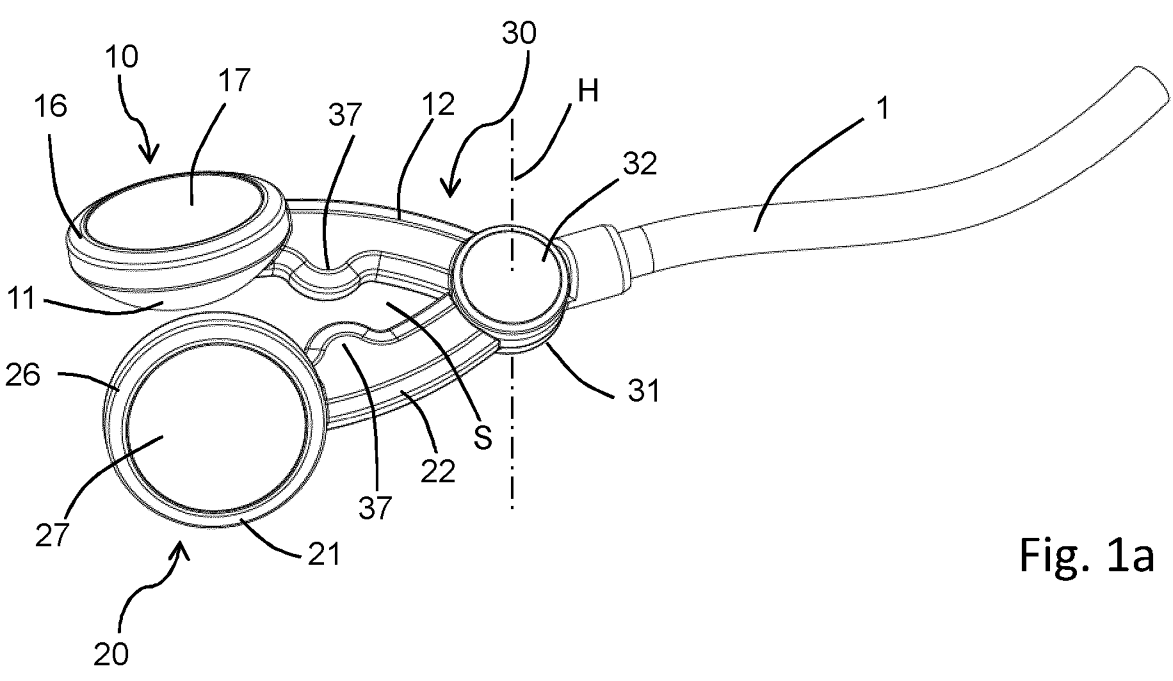
FIG. 1*a* shows a first embodiment of a stimulation device according to the present invention comprising a first coil unit, a second coil unit and a bracket structure in a narrow configuration.
Figure 1B:
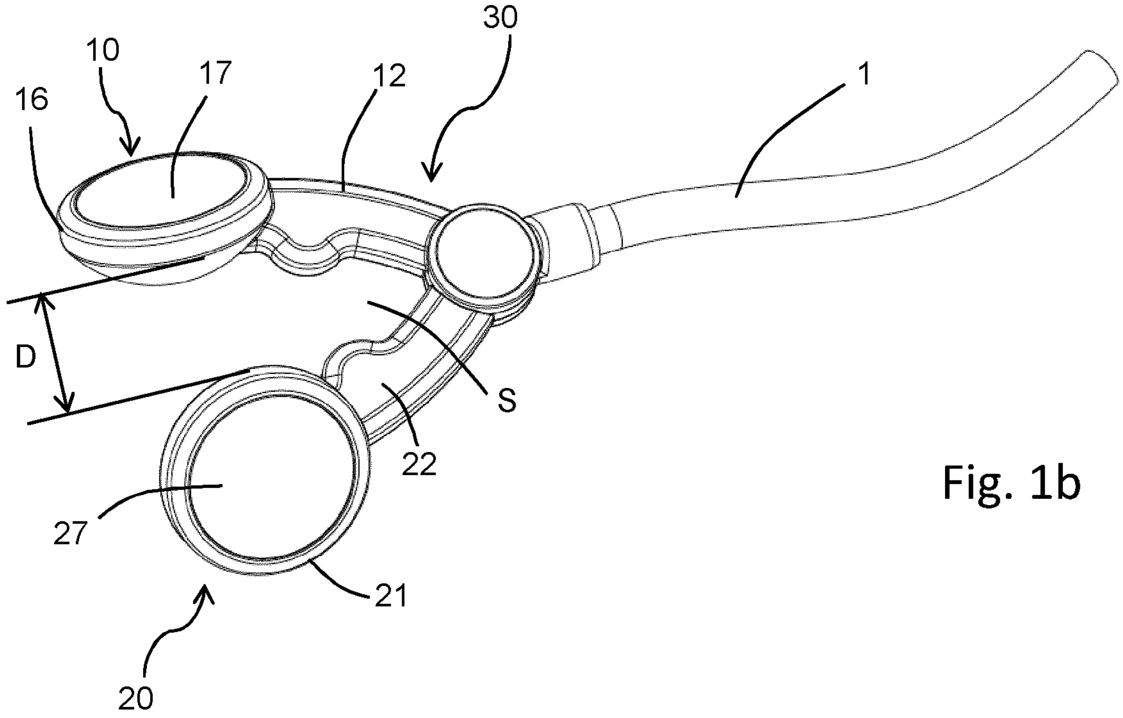
FIG. 1*b* shows the first embodiment of a stimulation device in a wide configuration.

FIGS. 1*a* and 1*b* illustrate a first embodiment of a stimulation device to coordinately stimulate two nerves of a patient—a human or an animal—for activating a target tissue of the patient. The stimulation device comprises a first coil unit 10 having a first forward face 11 configured to be positioned at the patient to stimulate a first nerve of the patient and a second coil unit 20 having a second forward face 21 configured to be positioned at the patient to stimulate a second nerve of the patient.

Advantageously, the coil units 10, 20 may comprise a housing 16, 26 for accommodating the associated coil winding 13, 23 and providing contact surfaces to be positioned at the patient. The first coil unit 10 has a first housing 16 encasing a first coil winding 13 and the second coil unit 20 has a second housing 26 encasing a second coil winding 23. By such housings 16, 26 the coil windings 13, 23 of the coil units 10, 20 can be encased and protected. Also, the housing 16, 26 with the coil winding 13, 23 safely positioned and precisely oriented therein allows for assuring correct positioning and orienting of the coil winding relative to the patient and relative to each other. Further, the housings 16, 26 can provide suitable surfaces for the forward faces of the coil units, for example to be positioned at the patient. Thus, a surface of the first housing 16 serves as the first forward face 11 of the first coil unit 10 and a surface of the second housing 26 serves as the second forward face 21 of the first coil unit 20. Furthermore, the housings may carry a shielding as will be explained in more detail below.

The stimulation device further comprises a bracket structure 30 coupled to the first coil unit 10 and the second coil unit 20. Advantageously, the coil units 10, 20 can be detachably coupled to the bracket structure 30. In this case, the bracket structure 30 can easily be replaced or disposed in case needed.

The bracket structure 30 is releasably connected to a current supply cable 1 for coordinatedly providing current to the first and the second coil units 10, 20 for generating electro-magnetic fields such that the first nerve and the second nerve of the patient are stimulated and a target tissue of the patient is homogeneously activated. For generating the electro-magnetic fields, the first and the second coil units 10, 20 may advantageously each comprise a non-flat coil winding 13, 23 as described with respect to FIGS. 5 to 7. However, conventional flat coil windings may be used as well without departing from the present invention or foregoing any of the benefits of the invention. The elongate component can for example be a metal wire such as a copper wire or the like.

The coil windings 13, 23 can be positioned and fixed within the housings 16, 26 of the coil units 10, 20 such that a side of the coil winding 13, 23 that is determined to face towards the patient is oriented towards the housing surface providing the forward face 11, 21 of the respective coil unit 10, 20. In case of non-flat coil windings, as for example a convex coil winding as further described below, the housing 16, 26 may have a similar three-dimensional shape as the coil windings 13, 23. Thus, the orientation of the non-flat coil winding 13, 23 towards a patient can be visually monitored in a simple manner. For example, the housings 16, 26 shown in FIGS. 1 to 4 have a flat surface representing backward faces 17, 27 of the coil units 10, 20, and a bulged surface representing forward faces 11, 21. Further, circumferential sides of the housing 16, 26 connect the backward facing surface and the forward facing surface.

The bracket structure 30 is adjusted such that positions and orientations of the first coil unit 10 and of the second coil unit 20 are adapted to the specific needs of a patient and for generating an electro-magnetic field targeted for stimulating the two separate nerves of the patient for activating a target tissue. The bracket structure 30 has a third forward face 31 configured to be positioned at the body of the patient. The stimulation device is configured to be arranged at a defined location of the patient when the first forward face 11, the second forward face 21 and the third forward face 31 are positioned at the patient in a chosen configuration of the bracket structure 30 suitable for the specifics of the treatment of the patient. Thus, the positioning and angle adjustment of the three forward faces 11, 21, 31 define a target configuration of the stimulation device.

In use, the stimulation device is arranged at a defined location of the patient such that the first forward face 11, the second forward face 21 and a third forward face 31 are in contact with the patient. When being positioned at the body, the three forward faces serve as three support points and determine defined contact points on the body. Like this, the stimulation device can be stably and precisely positioned with respect to the patient's nerves, and at the same time provides access to other important areas of the patient. The electro-magnetic field generated by the first and the second coil units 10, 20 can be precisely targeted to their respective target nerve without implying co-stimulation of other body tissue.

In the embodiment shown in FIGS. 1*a* and 1*b*, the bracket structure 30 comprises a first leg portion 12, a second leg portion 22 and a hinge portion 32 connecting the first leg portion 12 and the second leg portion 23 with each other. In this embodiment the first leg portion 12 and the second leg portion 22 are realized as flat rod elements having a curved shape. The first coil unit 10 is releasably coupled to one end of the first leg portion 12 and the second coil unit 20 is releasably coupled to one end of the second leg portion 22. The hinge portion 32 is arranged at an opposing end of the first and second leg portion 12, 22 and flexibly couples the first and second leg portions at their opposing ends.

Figure 4:
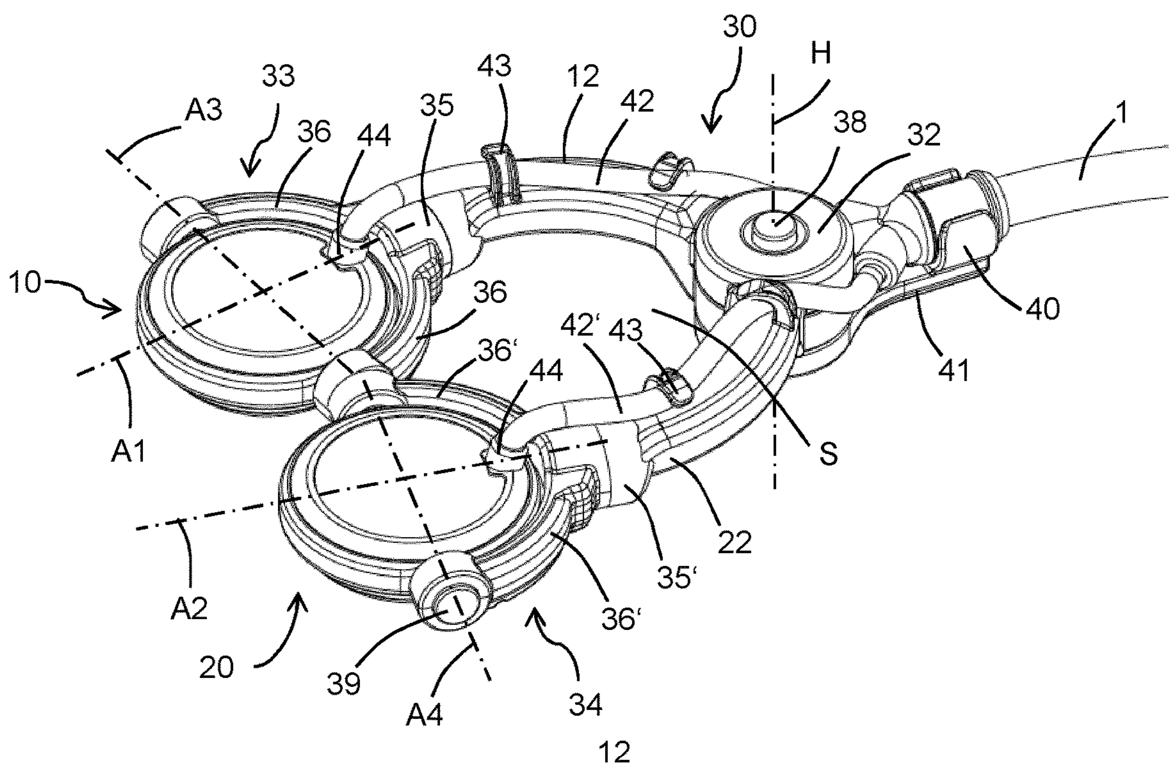
FIG. 4 shows a fourth embodiment of a stimulation device according to the present invention comprising a first coil unit, a second coil unit and a bracket structure with a pivoting coupler for mounting the coil units.

Further, the rod elements serving as the first and second leg portions 12, 22 each comprise a bulge 39 that extends from a middle section of the rod elements. The bulges 39 may serve for manually handling and adjusting the bracket structure 30. Also, the rod elements may each comprise a fixation arrangement for releasably holding a current line that runs along the leg portion and connects the current supply cable 1 at one end of the leg portions to the coil units 10, 20 at the other end of the leg portions 12, 22. An example for a fixation arrangement is shown in FIG. 4.

In the embodiment of FIGS. 1*a* and 1*b*, the hinge portion 32 is configured as a pivot bearing such that the first and second leg portions can be pivoted around a common articulation axis H of the bearing that runs through the centre of the hinge portion 32. Thus, the leg portions 12, 22 can be swivelled around the axis H in a common two-dimensional plane. Alternatively, the hinge portion 32 could provide more than one articulation axis for adjusting the leg portions 12, 22 three-dimensionally. In this case, the hinge portion 32 could for example be configured as a ball bearing.

The hinge portion 32 allows for adjusting a distance D between the first coil unit 10 and the second coil unit 20 to adapt the position and orientation of the first and second coil units according a desired target configuration of the bracket structure 30 depending on the requirements for use of the stimulation device. FIG. 1*a* shows the stimulation device in a narrow configuration of the bracket structure 30, wherein the first coil unit 10 and the second coil unit 20 are in a short distance D from each other. FIG. 1*b* shows the stimulation device in a wide configuration of the bracket structure with a larger distance D between the first coil unit 10 and the second coil unit 20.

The curved shape of the first leg portion 12 and the second leg portion 22 guaranties that in any pivoting position of the first leg portion 12 and the second leg portion 22 relative to each other a free space S is provided between the hinge portion 32 and the first leg portion 12 and the second leg portion 22. However, the free space S of the narrow configuration of the bracket structure provides a smaller free area between the leg portions 12, 22 than the wide configuration. When for example stimulating the two Phrenic nerves, the free space provides ample access to a front area of a neck of a patient that is commonly important for treatment of the patient such as a tracheotomy. The leg portions 12, 22 shown in FIGS. 1*a* and 1*b* are curved in one geometrical plane. However, additionally they could be curved in a second geometrical plane, for example perpendicular to the one plane. Thus, they could create an arch providing additional free space and access to the patient, for example from the sides of the neck.

Advantageously, the stimulation device rests on the body surface of the patient only with the three forward surfaces 11, 21, 31 located at the first coil unit 10, the second coil unit 20 and at the bracket structure 30. Thus, the three forward surfaces 11, 21, 31 provide support points in a triangular geometry. This enables stable and well-defined positioning at the patient independent of an individual surface landscape of the patient's body while space constraints can be overcome and the stimulation device can be carried by the patient conveniently and pain-free. Further, the geometry of the bracket structure determines a target configuration of the stimulation device and determines a defined location and orientation of the coil units generating the electro-magnetic fields for activating the target tissue. This results in efficient stimulation of both nerves and avoids co-stimulation effects on tissue in the vicinity of the two nerves, particularly in between the two Phrenic nerves where the field could interfere with other medical treatment.

Figure 2:
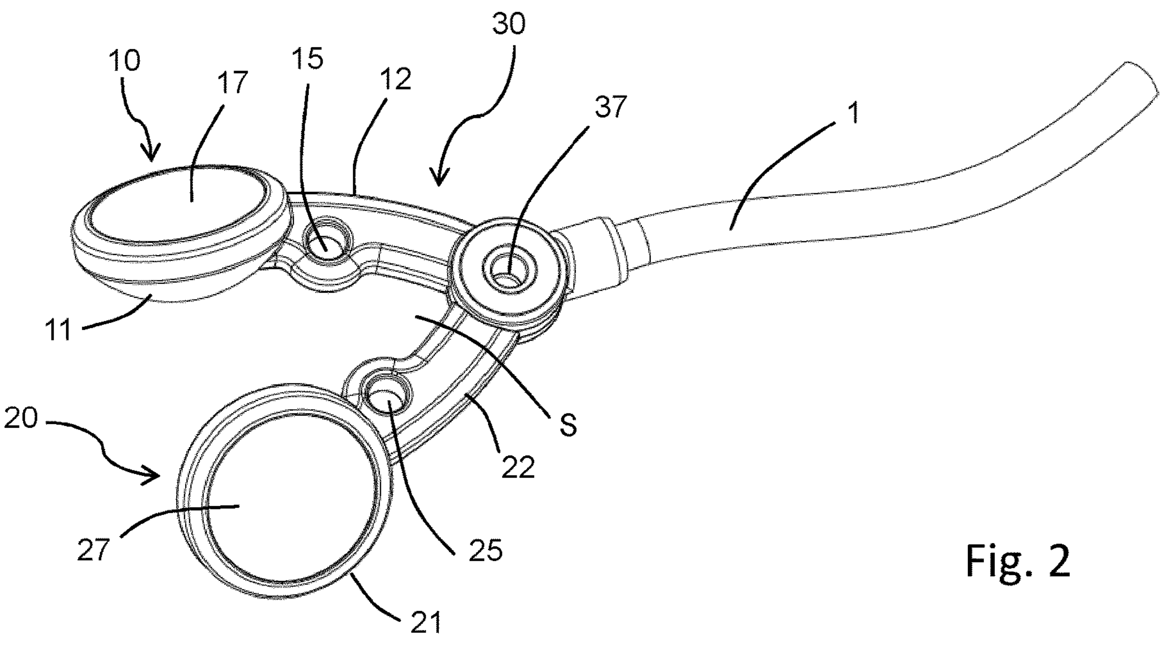
FIG. 2 shows a second embodiment of a stimulation device according to the present invention comprising a reference structure.
Figure 3:
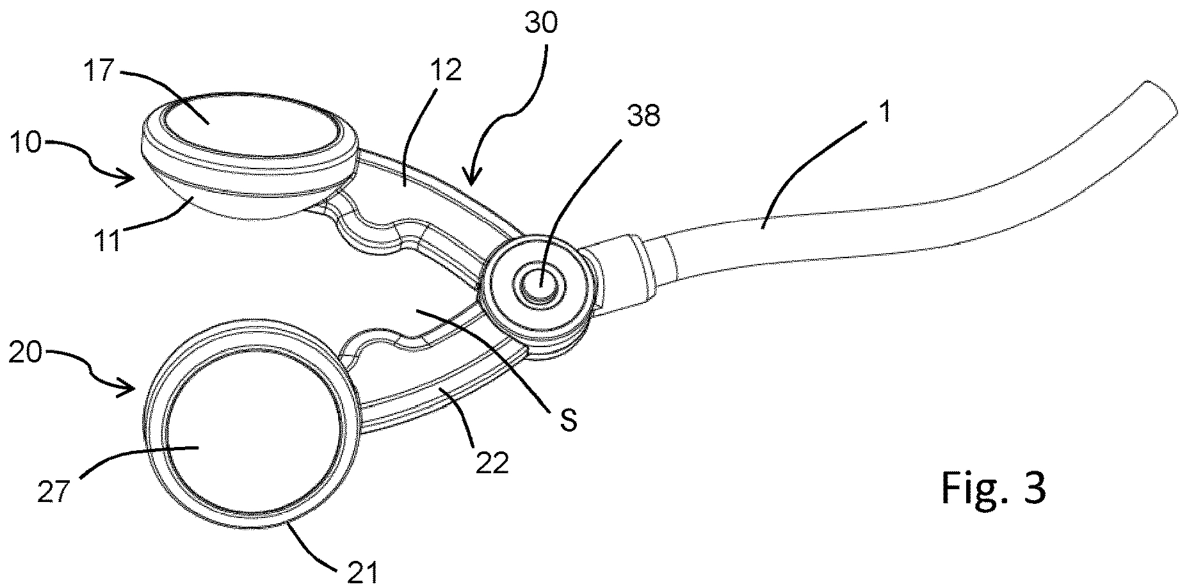
FIG. 3 shows a third embodiment of a stimulation device according to the present invention comprising a locking mechanism.

The embodiments of the stimulation device according to the invention as shown in FIGS. 2 to 4 are generally configured analogue the embodiment of FIG. 1 but include additional or alternative features to amend the use of the stimulation device as described in the following.

In a second embodiment illustrated in FIGS. 2, the stimulation device comprises a reference structure in form of through-holes. The bracket structure 30 comprises a through-hole 15 in the first leg portion 12, a through-hole 25 in the second leg portion 22 and a through-hole 37 in the hinge portion 32. The reference structure is configured to repeatedly locate the stimulation device at the defined location of the patient's body. The through-holes 15, 25, 37 allow to align the bracket structure with a specific portion of the body such as at a landmark thereof. By having the reference structure and for example using the natural landmarks of the body, the stimulation device can conveniently be re-positioned at the body such that it can be assured that the first and second coil units 10, 20 are properly positioned and oriented to stimulate the first and second nerves.

Further, the through-holes 15, 25, 37 can be designed to provide markers to the patient's body there through, when the stimulation device is in a desired target configuration. The markers can, for example, be provided by a pen or similar item applying a visual sign on the patient's body. Thus, the markers on the patient's body assist to properly position and orient the first and second coil units 10, 20.

The natural body landmarks and/or the markers also may assist in re-adjusting the bracket structure 30 to an already known suitable target configuration. The position and orientation of the coil units 10, 20 can be re-adapted by moving the leg portions 12, 22 to align the landmarks and/or markers with the through-holes 15, 25, 37. Thus, in use of the stimulation device the bracket structure can easily be exchanged.

In a third embodiment of a stimulation device according to the present invention illustrated in FIGS. 3, the bracket structure 30 comprises a locking mechanism to block the position and orientation of the first coil unit 10 and the second coil unit 20 relative to each other in the target configuration of the bracket structure. The locking mechanism can for example be provided by a mechanical mechanism or an electrical arrangement.

In the shown embodiment, the locking mechanism is realized by a bracket locking structure 38, for example in form of a locking button, which blocks rotation of the first leg portion 12 and the second leg portion 22 in the hinge portion 32 of the bracket structure 30 upon activation of the bracket locking structure 38. The bracket locking structure 38 can block the movement of the leg portions 12, 22 for example by providing a form fit within the hinge portion 32 in a pushed in or turned position. Alternatively or additionally, the bracket locking structure 38 could block the leg portions 12, 22 by frictional locking. The locking mechanism can prevent changes of the configuration of the bracket structure 30 after the target configuration has been adjusted, which guarantees adequate stimulation of the nerves by the stimulation device. Thus, the stimulation device can be removed from the patient and replaced at a later point in time without the need of recalibration of the coil units.

The locking mechanism of the bracket structure 30 can be configured to irreversibly block the position and orientation of the first coil unit 10 and the second coil unit 20 relative to each other in the target configuration of the bracket structure 30. By irreversibly blocking the bracket structure the target configuration cannot accidentally be changed whereby a re-adjustment of the stimulation device would become necessary.

In a fourth embodiment of the stimulation device shown in FIG. 4, pivoting coupler 33, 34 are used to adjust orientation of the first coil unit 10 and the second soil unit 20. Further, the pivoting coupler 33, 34 can be blocked by a locking mechanism according to the invention. The locking mechanism of the bracket structure 30 according to the invention is configured to block the orientation of the first coil unit 10 and the second coil unit 20 adjusted by the pivoting coupler 33, 34 relative to each other in the target configuration of the bracket structure 30

The coil units 10, 20 are coupled to the bracket structure 30 using U-like shaped pivoting couplers, which are detachably mounted to the bracket structure 30. The U-shape is realized by a stem portion 35 and two symmetrically curved branch portions 36 of the pivoting couplers. Alternatively, the pivoting couplers could have Y-like shape, a ring-shape or any other suitable shape for pivotably bearing the coil units.

As shown in FIG. 4, a first pivoting coupler 33 has a stem portion 35 and two branch portions 36, and a second pivoting coupler 34 has a stem portion 35' and two branch portions 36'. The stem portion 35 of the first pivoting coupler 33 is mounted to an end of the first leg portion 12 and the stem portion 35' of the second pivoting coupler 34 is mounted to an end of the second leg portion 22. The pivoting couplers 33, 34 basically are arranged in extension of the leg portions at an end thereof. The first coil unit 10 is mounted between the two branch portions 36 of the first pivoting coupler 33 and the second coil unit 20 is mounted between the two branch portions 36' of the second pivoting coupler 34.

The first pivoting coupler 33 is pivotably mounted to the first leg portion 12 such that the first pivoting coupler 33 can be pivoted relative to the first leg portion 24 about an axis A1 of the first leg portion 12. Respectively, the second pivoting coupler 34 is pivotably mounted to the second leg portion 22 such that the second pivoting coupler 34 can be pivoted relative to the second leg portion 22 about an axis A2 of the second leg portion 22. The leg portion axes A1 and A2 are basically aligned with the longitudinal direction of the end portions of the curved leg portion elements and the longitudinal axis of the stem portion 35 of the pivoting couplers. Thus, depending on an adjustment angle of the first leg portion 12 and the second leg portion 22 relative to each other at the hinge portion the leg portion axis A1 and the leg portion axis A2 can enclose different angles. However, pivoting the first coil unit 10 around axis A1 and pivoting the second coil unit 20 around axis A2 can cause the coil units 10, 20 to face more towards or more away from each other in most hinge portion adjustment angles. This can for example result in an increase or decrease of an overlap of the electro-magnetic fields generated by the coil units 10, 20, respectively, and facilitate the alignment of the electro-magnetic fields with the position of the two nerves.

In the shown embodiment, the first and second coil units 10, 20 are also pivotably mounted between the branch portions 36 such that the first coil unit 10 can be pivoted relative to the first pivoting coupler 33 about an axis A3 and the second coil unit can be pivoted relative to the second pivoting coupler 34 about an axis A4. The axes A3 and A4 basically connect the ends of the branch portions 36, 36' of the respective pivoting coupler.

In summary, the axes A1, A2 along the longitudinal axis of the stem portion 35 define first articulation axes of the pivoting couplers, and the axes A3 and A4 crossing the ends of the branch portions 36, 36' within each pivoting coupler define second articulation axes of the pivoting couplers. The first and second articulation axes are essentially perpendicular to each other. Therefore, the coil units 10, 20 can be adjusted in any three-dimensional direction and accordingly an electro-magnetic field generated by the coil units can be provided in any area required for an optimized stimulation field targeting both of the nerves. The angle adjustment of the first and the second coil units 20 for optimized orientation of the coil units 10, 20 can be performed individually according to specific needs of the patient and for generating the targeted electro-magnetic field for stimulating the two nerves of the patient. Thus, negative side effects during the treatment can be avoided and contact points convenient for the patient can be found.

After adjusting the orientation of the first and second coil units 10, 20 by choosing a suitable angle adjustment relative to each other and relative to the patient, the locking mechanism according to the invention blocks the movement of the coil units 10, 20 within the pivoting couplers 33, 34. The locking mechanism is realized by a branch locking structure 39, for example having a push button, which blocks the movement of the coil units 10, 20 in the adjusted angel position in the pivoting couplers 33 and 23 upon activation of the branch locking structure 39. The blocking structure for blocking such movement can be a mechanical locking structure, which provides blocking after pushing in or rotating the branch locking structure 39. Again, the blocking structure can provide a form fit, a friction blocking or a combination thereof.

Further, in the shown embodiment the locking mechanism according to the invention comprises a stem locking structure 39' suitable to block an orientation of the pivoting coupler 33, 34 relative the leg portions 12, 22 of the bracket structure 30.

Figure 5:
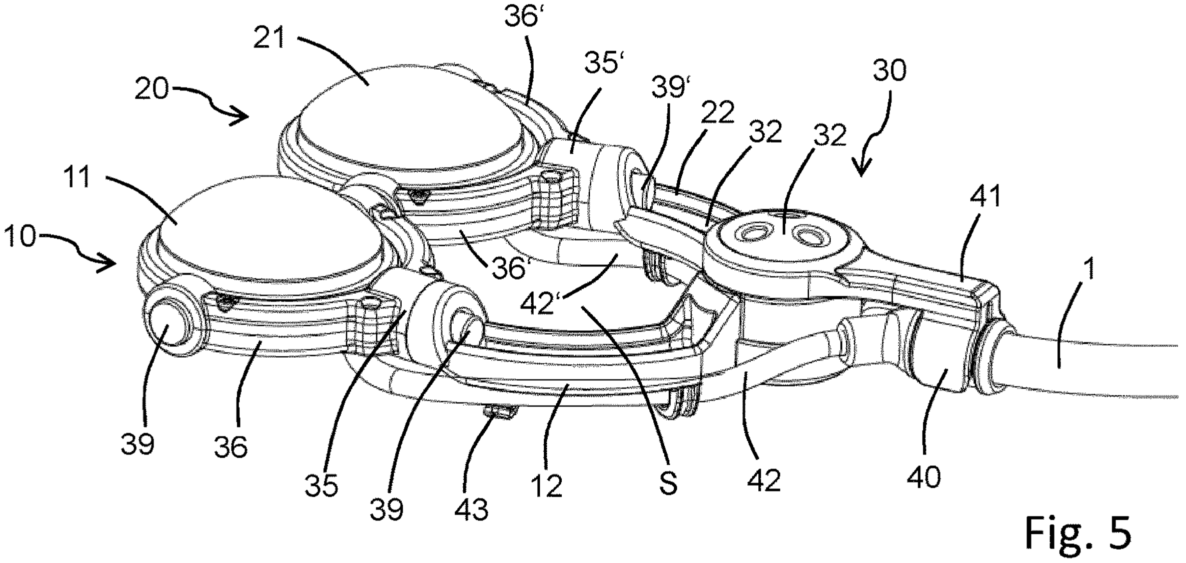
FIG. 5 shows a fifth embodiment of a stimulation device according to the present invention comprising a first coil unit, a second coil unit and a bracket structure with a locking mechanism comprising mechanical push buttons.

FIG. 5 shows the embodiment of FIG. 4 in a turned around position, wherein the forward face 11 of the first coil unit 10 and the forward face 21 of the second coil unit 20 are at an upper side of the stimulation device. As can be seen, the forward faces 11 and 21 have a concave, bulged surface.

As can be seen in FIG. 5, each of the pivoting couplers 33, 34 comprises a stem locking structure 39', which is arranged at an end portion of the leg portions 12, 22, respectively. Alternatively, the stem locking structure 39' could be arranged at the stem portions 12, 22 itself. The stem locking structure 39' is realized with a push button and blocks movement of the stem portion 35, 35' relative to the leg portion 12, 22 carrying the stem portion. To block such movement again the stem locking structure 39' may be pushed in or rotated, and the stem locking structure 39' can provide a form fit, a friction blocking or a combination thereof.

Overall, in the illustrated embodiment of the stimulation device, the locking mechanism of the bracket structure 30 to block the position and orientation of the first coil unit 10 and the second coil unit 20 relative to each other in a target configuration comprises the bracket locking structure 38, two branch locking structure 39, one for each branch portion 36, 36', and the stem locking structure 39'. The locking structures 38, 39, 39' act along the hinge axis H, the leg axes A1, A2, and the coupler axes A3, A4. Alternatively, the locking structures could be realized for example as abutment structures acting between the moving parts of the bracket structure. Of course, any other locking structure suitable for blocking position and orientation of the coil units 10, may be used.

Advantageously, all of the locking structures may be designed to irreversibly block the position and orientation of the first and the second coil units 10, 20. Thus, a stimulation device can be customized to an individual patient by personalizing the bracket structure of the stimulation device. Nevertheless, the coil units 10, 20 and the supply cable 1 can be detachably coupled to the bracket structure 30. Therefore, the coil units 10, 20 and the supply cable 1 can be used with another bracket structure.

The current supply cable 1 is releasably held in a clip mounting 40 arranged at an extension plate 41 extending from the hinge portion 32. The supply cable 1 feeds two current lines 42, 42', which run along the bracket structure 30 and provide current pulses to the first coil unit 10 and the second coil unit 20. The current lines are detachably fixed to the leg portions by fixation fingers 43. The current lines 42, 42' are connected to the coil units by common connectors 44. The supply cable 1 and the current lines 42, 42' can be detached from the bracket structure 30 and from the coil units 10, 20. Thus, they can be used with a different bracket structure and different coil units 10, 20 and the stimulation device can easily be modified for different use situations. For example, the bracket structures can be embodied as disposables associated to a specific patient and to be replaced after treatment of the specific patient.

Advantageously, in a stimulation device according to the present invention the coil units are shielded to reduce or avoid generating an electro-magnetic field in other areas than needed for stimulation of the nerves. Therefore, at least the backward face 11 of the first coil unit 10 and the backward face 21 of the second coil unit 20 are shielded. By shielding the backward faces of the coil units and the coil windings, respectively, it can be prevented that persons or other medical devices are exposed to an electromagnetic field backwardly diverging from the coil units. The shielding can be provided at the housings 16, 26 of the coil units 10, 20. Shielding material can be attached to the housing or the housing it self may be made of material with shielding properties at surfaces requiring shielding. Accordingly, at least the backward housing surface has a shielding to prevent field components away from the patient.

Preferably, also lateral faces of the first coil unit 10 and the second coil unit 20 are shielded. In the embodiments of coil units presented, their lateral faces match with the circumferential side of the housing, which connects the backward surface and the forward surface of the housing. As a result, the coil units generate an electro-magnetic field only in forward direction areas towards a patient. Each of the coil units nether produces field components in areas backwards nor sideward towards the other of the two coil units. Therefore, the electro-magnetic fields of the two coil units only may overlap in their forward direction to create a targeted field for stimulating the two nerves, which helps to control the overall electro-magnetic field provided by the stimulation device.

For example, the backward and/or lateral faces of the coil units can be shielded by a passive shield such as a u-Metal, a SCM, a passive coil winding, or the like. More advanced, the stimulation device may comprise an active shielding member configured to shield the backward faces of the first coil unit and the second coil unit. The active shielding member can comprise coil windings configured to cancel out field and/or change of field direction. For example, the shielding member can comprise a coil winding with a synchronized current in opposing direction with respect to the first or second coil windings 13, 23 of the coil units 10, 20. The active shielding members may conveniently be positioned within the housings 16, 26 of the coil units 10, 20.

As an possible example for an application of a stimulation device having a bracket structure with a locking mechanism, FIGS. 6 and 7 illustrate concepts of a stimulation device to coordinatedly stimulate two Phrenic nerves of a patient for activating a diaphragm of the patient. Generally, the stimulation device can be designed for example like any of the embodiments of a stimulation device shown in FIGS. 1 to 5. Therefore, like reference numbers in the figures represent the same elements or elements with similar function. Again, the stimulation device comprises a first coil unit 10 configured to be positioned at the patient to stimulate a first nerve of the patient, and a second coil unit 20 configured to be positioned at the patient to stimulate a second nerve of the patient.

The first coil unit 10 has a non-flat first coil winding 13 formed from a conductive elongate component and the second coil unit 20 has a non-flat second coil winding 23 also formed from a conductive elongate component. Each of the coil windings is formed by a plurality of spiral-like or helically wound turns of the conductive elongate component around a winding axis C of the coil winding. Successive turns decrease in radius starting from an outermost turn towards an innermost turn close to the winding axis. Furthermore, at least some of the turns are shifted along the winding axis to realize a non-flat shape of the first and second coil winding. Therefore, the first and the second coil winding are designed as three-dimensional bodies as can be seen in FIG. 6.

As described before, the non-flat coil windings 13, 23 can be accommodated in housings 16, 26 of the coil units 10, 20. An outermost turn of the coil winding having the largest diameter is located towards the backward face of the housing. The innermost turn of the coil winding having the smallest diameter is located towards the forward face of the housing. Thus, the coil windings are positioned in the housings with their base side facing the backward facing surface of the housing. Correspondingly, their convex outward facing side is directed towards the forward facing surface of the housing. Thus, the base side of the coil windings 13, 23 corresponds to the backward faces 17, 27 of the coil units 10, 20 and the outer side of the convex area of the coil windings 13, 23 corresponds to the forward faces 11, 12 of the coil units 10, 20. By having the convex side of the coil windings directed towards the forward faces, it is achieved that in use of the stimulation device, the convex sides of the coil windings are directed tot the patient. Therefore, such housing guarantees precise positioning of the coil units with the coil winding at the patient.

Figure 6A:
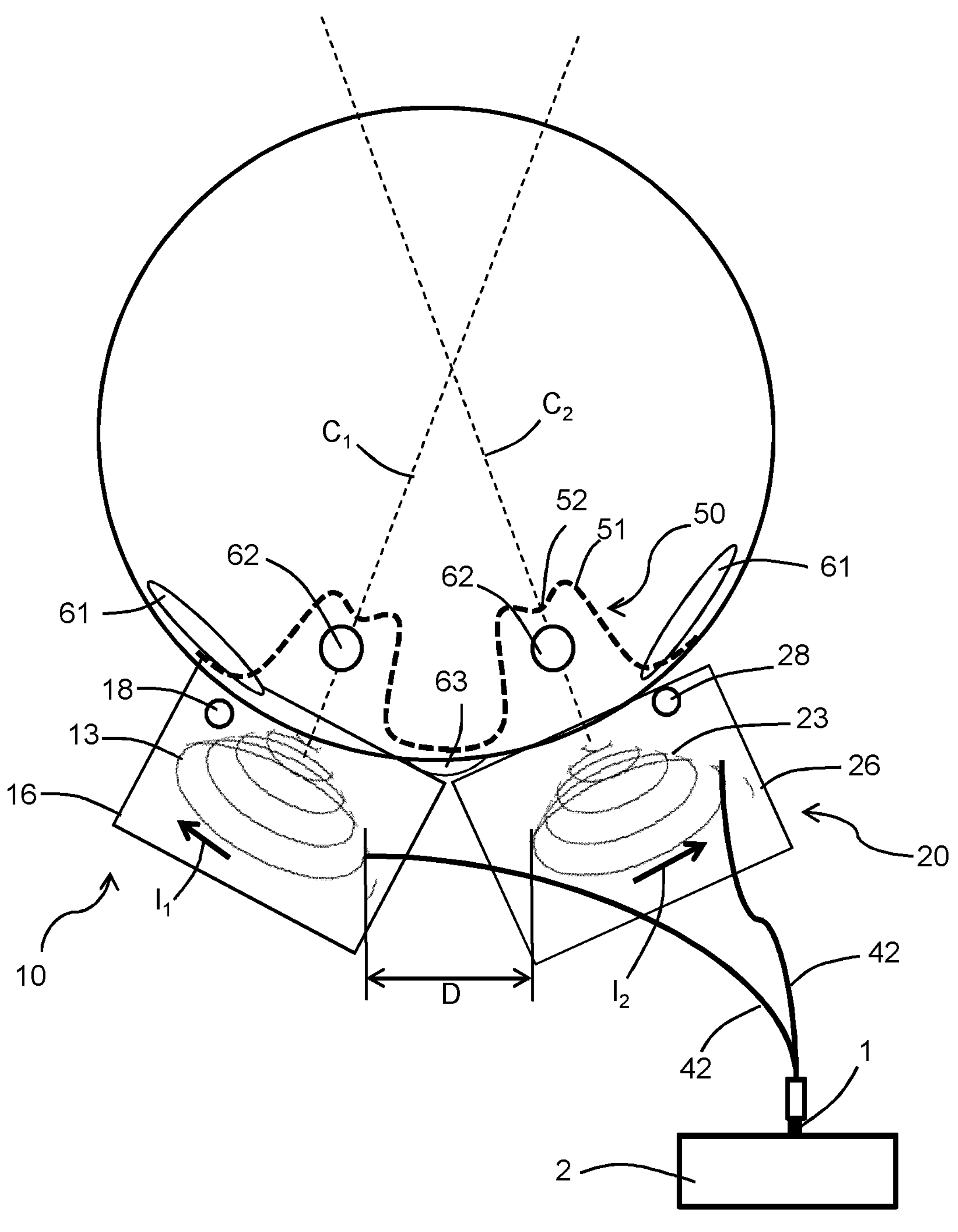
FIG. 6*a* shows a schematic view of the use of a stimulation device according to the present invention comprising a convex first coil winding and convex second coil winding.
Figure 6B:
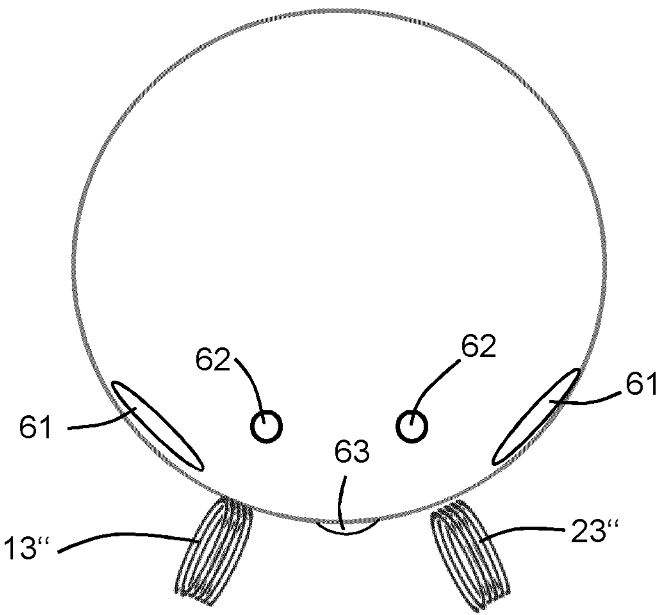
FIG. 6*b* shows a schematic view of the use of a stimulation device according to the present invention comprising a cylindrical first coil winding and a cylindrical second coil winding, wherein the coil windings are arranged with their cylindrical circumference on the body surface.
Figure 6C:
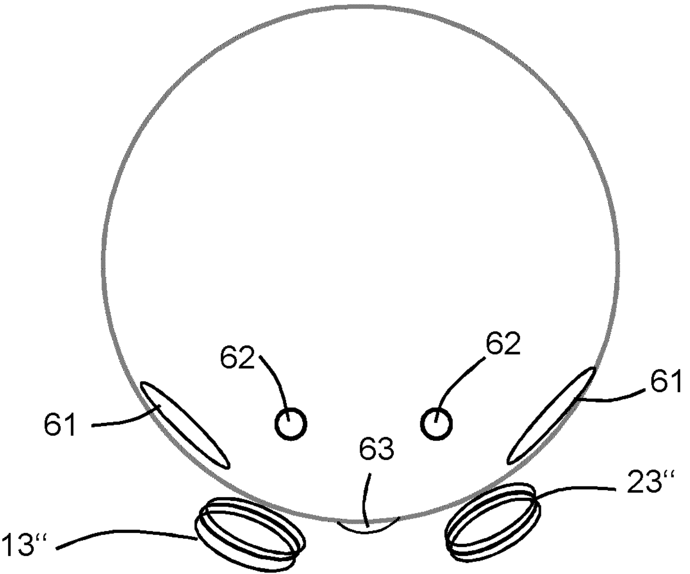
FIG. 6*c* shows a schematic view of the use of a stimulation device according to the present invention comprising a cylindrical first coil winding and a cylindrical second coil winding, wherein the coil windings are arranged with their outermost coil winding on the body surface.
Figure 7A:
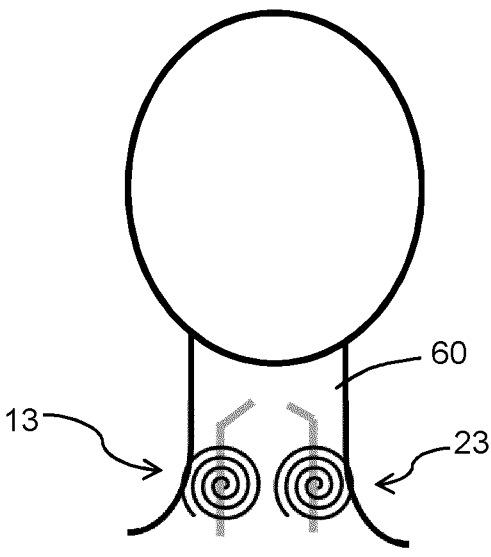
FIG. 7*a* shows a schematic view of a first coil winding and a second coil winding of the stimulation device comprising a circular base shape.
Figure 7B:
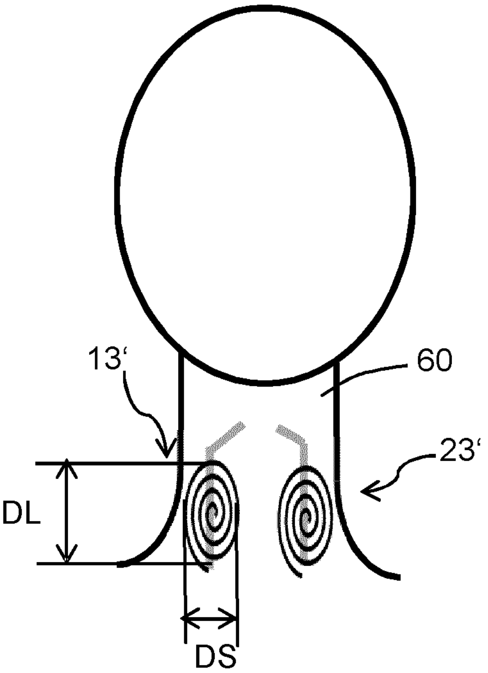
FIG. 7*b* shows a schematic view of a first coil winding and a second coil winding of the stimulation device comprising an oval base shape.

FIGS. 6 and 7 show a schematic view of embodiments of the stimulation device according to the present invention in use at a neck 60 of a patient seen; in FIGS. 6*a* to 6*c* from the top of the neck, and in FIGS. 7*a* to 7*d* from a front few onto the neck. FIGS. 6*a*, 7*a* and 7*b* show examples, wherein the coil windings have a convex shape, particularly an essentially conical shape. FIGS. 6*b*, 6*c*, 7*c* and 7*d* show examples, wherein the coil windings have a cylindrical shape.

In favour of a better comprehensibility, some of the components of the stimulation device are not illustrated in the figure. As mentioned before, the first coil unit 10 and the second coil unit 20 each comprise a conical coil winding 13, 23. The first coil unit 10 with the first coil winding 13 is placed at an anterior border of a right sternocleidomastoid muscle 61, and the second coil unit 20 with the second coil winding 23 is placed at an anterior border of a left sternocleidomastoid muscle 61, wherein the larynx 63 lies in between the two coil windings 13, 23. The first and the second coil windings 13, 23 are spaced apart in distance D from each other. The distance D can vary according to varying physiologies of different patients and different treatments provided for the patient. A first winding axis C1 of the first coil winding 13 and a second winding axis C2 of the second coil winding 23 converge in direction towards the patient. Preferably, the first and the second winding axis C1 and C2 at least approximately intersect with the respective Phrenic nerve associated to the coil windings 13, 23. Preferably, the first and the second winding axis C1 and C2 lie in a common plane, which facilitates optimizing the electrical field exerted on the Phrenic nerves.

Advantageously, a stimulation device comprising a bracket structure as discussed above is used for adjusting the positions and orientations of the coil units 10, 20 and blocking them in the target configuration. Therefore, the coil windings 13, 23 can reliably and repeatedly positioned at the patient by taking advantage of support points provided by the coil units or their housings respectively. The term, "positioned at" as used herein can relate to being located at a patient's body by contacting it. For example, the three forward faces of the stimulation device can be positioned at the body by lying on it. When being positioned at the body, the three forward faces can form three support points and determine defined contact points on the body. Like this, the stimulation device can be stably and precisely positioned with respect to the patient's Phrenic nerves. Further, by choosing a specific target configuration of the bracket structure and specific contact points on the patient's body a defined location of the stimulation device with respect to the patient is determined. The defined location is defined in that the first forward face, the second forward face and the third forward face provided at the bracket structure are in contact with the patient at a position optimized for stimulating the Phrenic nerves.

In case that coil unit positioning without a bracket structure as discussed before is chosen, only two support points may be available corresponding to the first forward face of the first coil unit and the second forward face of the second coil unit. However, positions and orientations of the coil units may for example be adjusted manually. Alternatively, a suitable support structure may be provided configured to hold the first and the second coil units in a pre-set or adjustable position and orientation towards each other, which are suitable for generating the targeted electro-magnetic field of the stimulation device.

The power supply 2 provides a current flow in the coil windings 13, 23 for example via a common current supply cable 1 and two current lines 42 running to each of the coil windings 13, 23. The power supply 2 may be connected to or may include a control unit configured to coordinatedly provide a current flow through to the first and second coil windings 13, 23. Preferably, the control unit is configured such that current is provided simultaneously to the first and the second coil windings 13, 23 according to a circulation direction for each of the coil winding required to generate a target electro-magnetic field suitable to stimulate the two nerves without impacting surrounding tissue.

In the example shown in FIG. 6*a* the winding directions of the two coil windings 13, 23 are identical. Therefore, the current direction is controlled by the control unit such that a flow direction of current $I_1$ in the first coil winding 13 is opposite to a flow direction of current $I_2$ in the second coil winding. Each of the coil windings 13, 23 generates an electro-magnetic field 50 targeted towards their associated Phrenic nerve 62. The two electro-magnetic fields 50 decrease toward an area in between the two coil windings, but any remaining overlap of the fields would result in mutual erasure of the fields and the resulting overall electro-magnetic field strength would be zero or near zero in this area. Consequently, for example the area around the larynx would not be affected by any electro-magnetic field generated by the stimulation device. When using a stimulation device having a bracket structure as discussed above, this area also is kept clear of any components of the device and is freely accessible for the treatment of the patient.

Alternatively to the convex shape of the coil windings 13 and 23 as shown in FIG. 6*a*, the coil winding could be realized as cylindrically shape coil windings 13" and 23". FIGS. 6*b* and 6*c* schematically illustrate the use of an embodiment of a stimulation device according to the invention having non-flat coil windings with a cylindrical shape. In FIG. 6*b*, a cylindrical first coil winding 13" and a cylindrical second coil winding 23" are arranged with their circumferential surface on the body surface with their winding axes arranged essentially perpendicular to an axis of the neck and the axes of the Phrenic nerves 62. In FIG. 6*c*, a cylindrical first coil winding 13" and a cylindrical second coil winding 23" are arranged with their circumferential surface on the body surface with their winding axes arranged essentially parallel to an axis of the neck and the axes of the Phrenic nerves 62. However, the first and the second coil windings 13" and 23" are preferably arranged in coil units coupled to a bracket structure as discussed for FIGS. 1 to 4 for positioning the apparatus at a patient and coordinatedly stimulating the two Phrenic nerves. Thus, position and orientation of the coil windings 13" and 23" can easily be fine-tuned relative to specific requirements of an individual patient. Adjusting the first and the second coil windings 13" and 23" by moving their coil units around the articulation axes of the bracket structure and then locking their positions will optimize the electro-magnetic field distribution for stimulating the Phrenic nerves.

Further, the first coil unit 10 comprise a first biofeedback sensor 18 and the second coil unit 20 comprises a second biofeedback sensor 28. The biofeedback sensors 18 and 28 are coupled to the control unit and the power supply, respectively. When the coil units 10, 20 are positioned at the patient, the biofeedback sensors 18 and 28 are oriented such that they can receive feedback signals from the Phrenic nerves and the diaphragm, respectively, when current is provided through the first and second coil windings 13, 23. For example, the first biofeedback sensor is positioned at the patient such that it provides a first feedback signal about contractility of a first diaphragm hemisphere, and the second biofeedback sensor is positioned at the patient such that it provides a second feedback signal about contractility of a second diaphragm hemisphere. Thus, the first coil winding 10 and the second coil winding 20 can be controlled coordinatedly in accordance with the first feedback signal and the second feedback signal and the power supply can individually provide a current to each of the coil windings 13, 23. For example, a current strength or a pulse frequency can be changed in response to the feedback signals such that the first and second nerves are stimulated and a diaphragm of the patient is homogeneously activated.

FIG. 7*a* shows a schematic example of coil windings 13, 23 as presented in FIG. 6*a* and their placement at the neck 60 of the patient. As illustrated, the coil windings basically have circular shaped turns. They are essentially symmetric around their winding axis, although of course the turns are linked spiral-like to form a winding. Their base shape as defined by their turn with largest diameter can be described as being circular. According to their shape, such coil windings generate an electro-magnetic field that is symmetric around a centre of the field and turning the coil unit around its winding axis will not change the field distribution in the areas around the coil unit.

In contrast to that, FIG. 7*b* shows a schematic example of coil windings 13', 23' comprising an oval shape and their orientation at the neck 60 of the patient. The turns of the coil windings 13', 23' are basically oval shaped. They are essentially symmetric to a plan including the winding axis. Their base shape as defined by their outermost turn is oval. Consequently, the outermost turn will have a large diameter DL in a first direction and a smaller diameter DS in a second direction perpendicular to the first direction.

The oval shape of the coil windings 13', 23' generates an oval shaped distribution of the electro-magnetic field produced by the coil units. A coil winding with an oval base shape produces an electro-magnetic field that is squeezed at opposing sides, when compared with the field produced by a coil winding of circular shape, if the large diameter DL of the oval shaped coil winding is equal to the diameter of the circular shaped coil winding. Consequently, the distribution of the electro-magnetic field of the oval shaped coil winding reaches less far in direction of the smaller diameter DS than in direction of the large diameter DL. Therefore, the electro-magnetic field resulting from the oval shaped coil winding can be more distant from tissue surrounding the Phrenic nerves while still reaching the nerves. Also, this allows positioning the coil units with oval shaped coil windings closer to such tissue than coil units with circular shaped coil winding without affecting such tissue. Advantageously, the two coil units 10, 20 are positioned such that their large diameters DL are parallel or nearly parallel to each other. For example, the first coil unit 10 having an oval shaped coil winding 13' and the second coil unit 20 having an oval shaped coil winding 23' can be placed closer to the sternocleidomastoid muscles, which may improve stimulation of the nerves without impacting the muscles and may provide more space between the first and the second coil unit 10, 20.

By providing coil windings with oval base shapes, oval electro-magnetic fields can be generated. Like this, the electro-magnetic fields can be longitudinally stretched such that, under certain circumstances, the electro-magnetic field can be better provided distant from muscular structures towards the nerves. For example, the longitudinally extending electro-magnetic fields facilitate the positioning of the coil units near or adjacent to the sternocleidomastoid muscles for stimulating the nerves. Like this, side effects in use of the apparatus can be lowered or prevented.

Figure 7C:
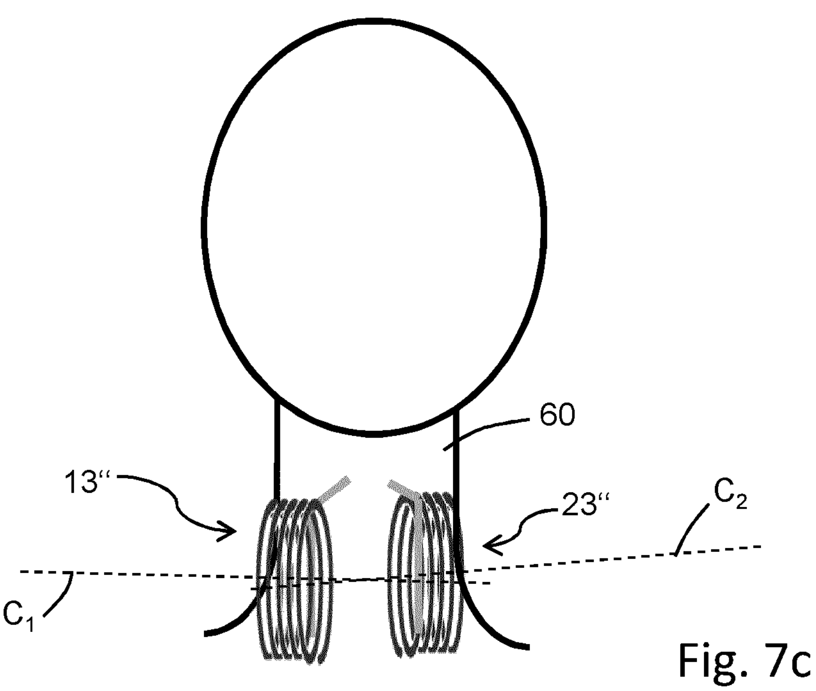
FIG. 7*c* shows a schematic view of a first cylindrical coil winding and a second cylindrical coil winding of the stimulation device arranged with their cylindrical axes essential perpendicular to a nerve axis.
Figure 7D:
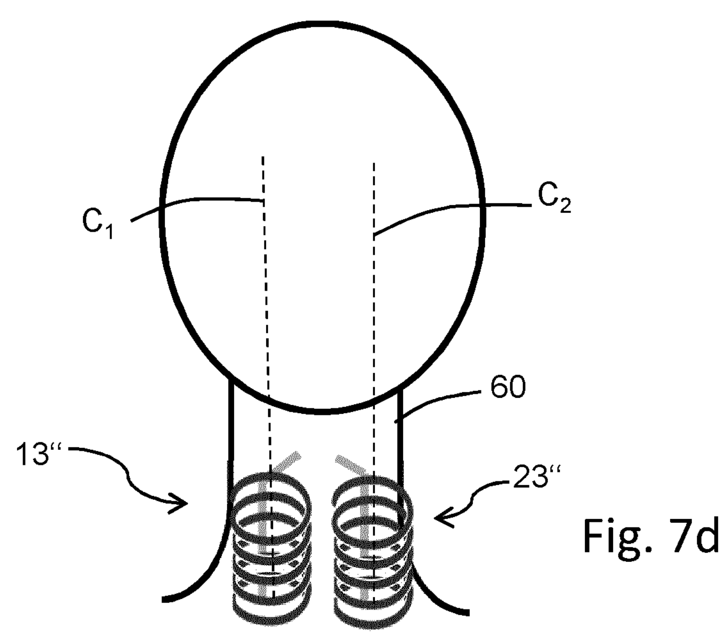
FIG. 7*d* shows a schematic view of a first cylindrical coil winding and a second cylindrical coil winding of the stimulation device arranged with their cylindrical axes essential parallel to a nerve axis.

FIGS. 7*c* and 7*d* shows a schematic examples of cylindrically shaped coil windings 13", 23" as presented in FIGS. 6*b* and 6*c* and their placement at the neck 60 of the patient. As illustrated, the coil windings basically have circular or oval shaped turns with identical diameters, and they are essentially symmetric along their winding axes $C_1$ and $C_2$. In FIG. 7*c*, the first and the second coil windings 13" and 23" are arranged with their circumferential surface towards the neck 60 of the patient. The winding axis $C_1$ of the cylindrical coil winding 13" and the winding axis $C_2$ of the cylindrical coil winding 23" are approximately perpendicular to an axis of the neck 60. In FIG. 7*d*, the first and the second coil windings 13" and 23" also are arranged with their circumferential surface towards the neck 60 of the patient. But their winding axes $C_1$ and $C_2$ are approximately parallel to an axis of the neck 60. However, the angles between the winding axes $C_1$ and $C_2$ can be adapted and also the angle between the winding axes $C_1$ and $C_2$ and the neck axis can be adapted for generating a targeted electro-magnetic field.

Figures 8, 9:
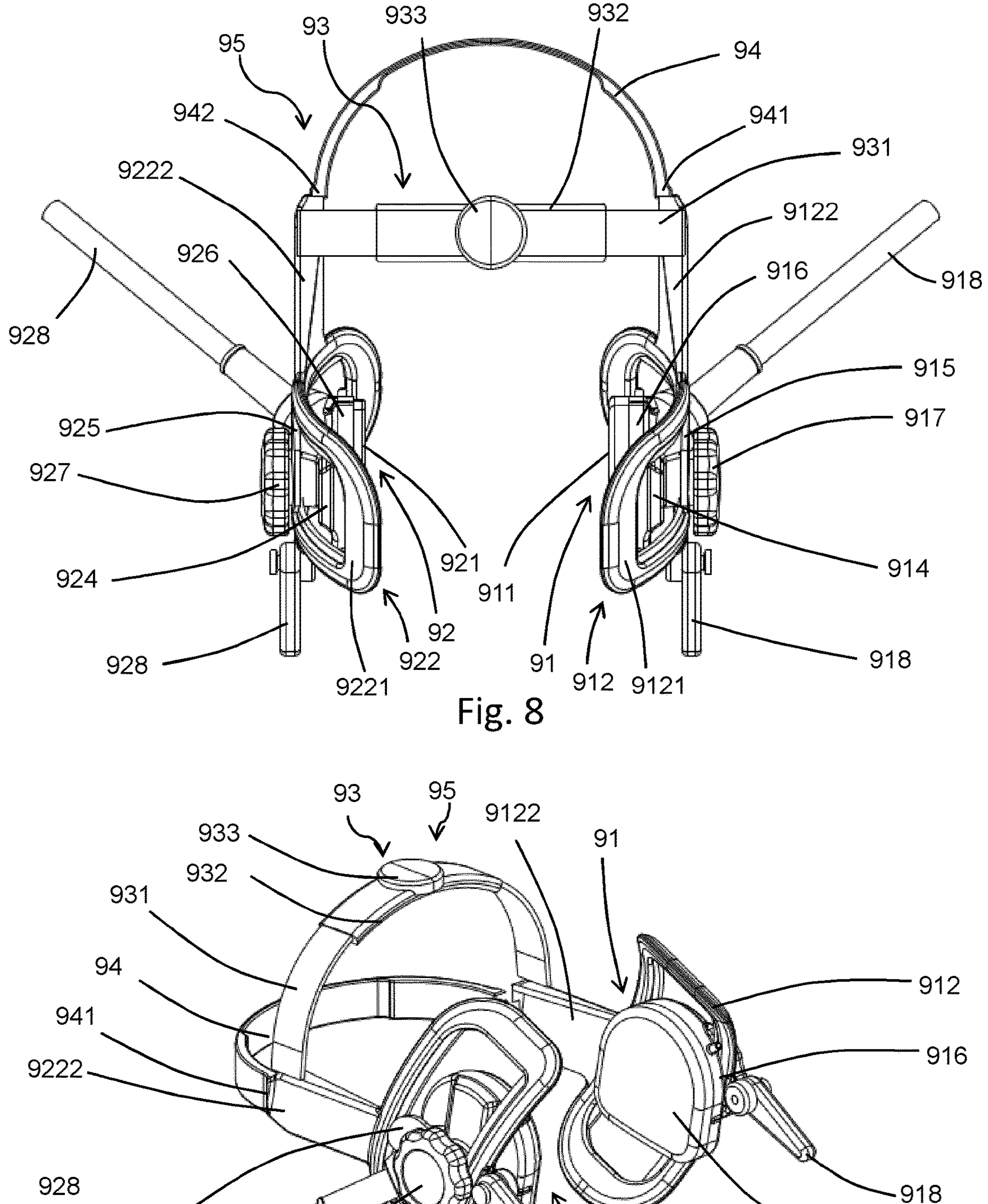
FIG. 8 shows a front view of a sixth embodiment of a respiration promoting apparatus according to the present invention.
FIG. 9 shows a perspective view of the respiration promoting apparatus of FIG. 8.

FIG. 8 shows a sixth embodiment of a stimulation device according to the invention, which is generally earphone-like shaped. The fifth stimulation device comprises a first coil unit 91, a second coil unit 92 and a bracket structure 95 to which the first and second coil units 91, 92 are coupled as described in more detail below.

The bracket structure 95 has an overhead arch 94 bent about 180°, a first frame portion 912 and a second frame portion 922. The overhead arch 94 forms a right-hand first tangential end 941 and a left-hand second tangential end 942. The first and second frame portions 912, 922 are essentially mirror symmetrically designed. The first frame portion 911 consist of a bent first rail section 9121 as first neck position guide section and a first height adjusting neck section 9122. Likewise, the second frame portion 921 consists of a bent second rail section 9221 as neck position guide section and a second height adjusting neck section 9222. The first and second height adjusting neck sections 9122, 9222 are essentially rod shaped and extend upwardly from the first and second rail sections 9121, 9221, respectively. At its top end, the first height adjusting neck section 9122 is connected to the first tangential end 941 of the overhead arch 94 and, at its top end, the second height adjusting neck portion 9222 is connected to the second tangential end 942 of the overhead arch 94.

In addition to the overhead arch 94, the first and second height adjusting neck sections 9122, 9222 are interconnected by a forehead support 93. The forehead support 93 comprises two bands 931 which are centrally connected via a sizing wheel mechanism 933. Further, at the sizing wheel mechanism 933 the forehead support is equipped with a support pad 932 forming a third forward face.

The first and second rail sections 9121, 9221 have a longitudinal opening in which a first guide member 915 and a second guide member 925, respectively, are slidably mounted. In particular, when not being fixed, the first and second guide members 915, 925 are slidable along the respective openings of the first and second rail sections 9121, 9221. The first coil unit 91 is mounted to the first guide member 915 by a first fastening screw 917 extending through a bore of the first guide member 915 and being screwed into a first screw socket 914 provided at a back side of the first coil unit 91. The second coil unit 92 is mounted to the second guide member 925 by a second fastening screw 927 extending through a bore of the second guide member 925 and being screwed into a second screw socket 924 provided at a back side of the second coil unit 91.

The first and second coil units 91, 92 have first and second housings 916, 926 inside each of which a litz wire is wound to form a coil. Further, the first coil unit 91 has a first forward face 911 and the second coil unit 92 has a second forward face 921, wherein the first and second forward faces 911, 921 are facing each other. To supply the coils of the first and second coil units 91, 92 with current, the first coil unit 91 is provided with a first current supply cable 918 and the second coil unit 92 is provided with a second current supply cable 928.

At a lower end side of the first rail section 9121 of the first frame portion 912, a first clavicula support bar 918 is pivotably mounted as support structure and at a lower end side of the second rail section 9221 of the second frame portion 922, a second clavicula support bar 928 is pivotably mounted as support structure. By being pivotably, the first and second clavicula support sections 918, 928 can be adapted to suit to a torso of a specific patient.

In FIG. 9 the fifth stimulation device is shown in perspective, in which it can be seen that the overhead arch 94 is essentially perpendicular to the forehead support 93. FIG. 10 shows the fifth stimulation device from a side.

In use of the fifth stimulation device, the first and second height adjusting neck sections 9122, 9222 are adjusted in length such that the overhead arch lies on the head of the patient. In particular, the length is adjusted such that the first and second rails sections 9121, 92221 extend about the left and right sides of the neck of the patient. Since the rail sections are bent 9121, 9222 they can run along the neck. The forehead support 93 is also adjusted in length by turning the sizing wheel mechanism 933 such that the central support pad 932 abuts the forehead of the patient. The first and second support rods 918, 928 are adjusted such that they rest on the left and right clavicles of the torso of the patient. In this configuration, the stimulation device is safely and stably mounted to the patient, wherein the two support rods 918, 928 and the forehead support 93 establish a robust three-point support.

Furthermore, the first and second guide members 915, 925 are slid along the first or second rail sections 9121, 9221 until the first and second forward faces 911, 921 of the first and second coil units 91, 92 are properly positioned at the neck of the patient to stimulate the two Phrenic nerves of the patient. Once being in an appropriate location and orientation, the first and second coil units 91, 92 are fixed to the first and second rail sections 9121, 9221 by tightening first and second fastening screws 917, 927. For allowing an efficient manual operation the first and second fastening screws 917, 927 are equipped with gripping portions. By tightening the first and second fastening screws 917, 927 the first and second coil units 91, 92 are outwardly pulled such that the respective rail section 9121 9221 is clamped between coil unit 91, 92 and guide member 915, 925. Like this, an efficient locking mechanism can be provided which allows to block the stimulation device in a configuration individually adjusted to the situation of the specific patient.

Altogether, the locking mechanism of the bracket structure 93 is formed by the first and second height adjusting neck sections 9122, 9222, by the sizing wheel mechanism 933, the first and second rail sections 9121, 9221, as well as by the first and second fastening screws 917, 927. By such locking structure, the device can be safely configured in a status where it suits an individual patient.

In FIGS. 11*a* and 11*b* a portion of a sixth embodiment of a stimulation device according to the invention is shown. In particular, FIGS. 11*a* and 11*b* exemplarily depict the mounting of a first coil unit 91 to a first rail section 9121' of a first frame portion 912'. The sixth stimulation device comprises a mirror symmetric coil second unit and mounting configuration. Furthermore, all elements of the sixth stimulation device not shown and described to be different are identical to the fifth stimulation device.

The first coil unit 91 is mounted to the first rail section 9121' via a first guide member 915'. Ata border of an opening of the first rail section 9121' a toothing 9123' is provided. Further, as can be seen in FIG. 11*b* where the first guide member 915' is not depicted, a first screw 917' comprises a cogwheel 9171' positioned under the first guide member 915'. The cogwheel 9171' engages the toothing 9123'. By turning the first screw 917' the gearwheel 9171' travels along the toothing 9123' such that the first guide member 915' and the first coil unit 91 are moved along the first rail section 9121. More specifically, the cogwheel 9171' snaps in the toothing 9123' at distinct positions defined by the toothing 9123'. Like this, the first coil unit 91 can conveniently be positioned and blocked at an appropriate location of the neck of the patient. The toothing 9123' and the cogwheel 9171' are comprised by the locking mechanism.

Using a stimulation device according the present invention comprising a bracket structure with a locking mechanism to block the position and orientation of the first and second coil units relative to each other allows for taking of the stimulation device of the patient, for example in case other treatments for the patient have priority. The stimulation device can easily be re-positioned and re-oriented in the defined location at the patient to continue stimulation of the nerves. Further unintended mis-adjustment is prevent, for example other treatments need to be taken care for.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known structures and techniques have not been shown in detail in order not to obscure the invention. Thus, it will be understood that changes and modifications may be made by those of ordinary skill within the scope and spirit of the following claims.

In particular, the present invention covers further embodiments with any combination of features from different embodiments described herein. For example, it is possible to operate the invention in an embodiment wherein:

- the stimulation device having a bracket structure is provided with non-flat coil winding, flat coil winding or a combination thereof;
- the stimulation device having a bracket structure may have a third leg portion for mounting a third coil winding and having a locking structure to block movement of the third leg portion;
- the stimulation device having non-flat coil windings may include additional coil windings in their respective coil unit; or
- the stimulation device having non-flat coil windings may be used with other support structures for mounting the coil units than the bracket structure.

Further, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately", "basically" and the like in connection with an attribute or a value particularly also define exactly the attribute or exactly the value, respectively. Any reference signs in the claims should not be construed as limiting the scope.

The invention claimed is:

1. A stimulation device to coordinatedly stimulate two separate Phrenic nerves in a human or an animal body for activating diaphragm in the human or the animal body, comprising:

- a first coil unit configured to be positioned at a neck of the human or the animal body to stimulate a first Phrenic nerve of the two separate Phrenic nerves;
- a second coil unit configured to be positioned at the neck of the human or the animal body to stimulate a second Phrenic nerve of the two separate Phrenic nerves; and
- a bracket structure coupled to the first coil unit and the second coil unit, wherein
- the bracket structure is adjustable such that positions and orientations of the first coil unit and of the second coil unit relative to each other are adaptable to a target configuration in which the first coil unit and the second coil unit are distinctly positioned at the neck of the human or the animal body such that the first Phrenic nerve can be stimulated by the first coil unit and the second Phrenic nerve can be stimulated by the second coil unit, and the bracket structure has a locking element to block the positions and orientations of the first coil unit and the second coil unit relative to each other in the target configuration.

2. The stimulation device of claim 1, wherein the locking element of the bracket structure is configured to irreversibly block the position and orientation of the first coil unit and the second coil unit relative to each other in the target configuration; or wherein the locking element of the bracket structure is configured to irreversibly block the position and orientation of the first coil unit and the second coil unit relative to each other in the target configuration, wherein the first coil unit and the second coil unit are detachably coupled to the bracket structure, and wherein the bracket structure is designed as a disposable.

3. The stimulation device of claim 1, wherein the bracket structure is configured to adjust a distance between the first coil unit and the second coil unit to a target distance of the target configuration; or wherein the bracket structure is configured to adjust a distance between the first coil unit and the second coil unit to a target distance of the target configuration, and wherein the locking element of the bracket structure is configured to mechanically prevent adjustment of the distance between the first coil unit and the second coil unit.

4. The stimulation device of claim 3, wherein the bracket structure comprises a first leg portion and a second leg portion connected to each other by a hinge portion, the first coil unit is coupled to the first leg portion and the second coil unit is coupled to the second leg portion, and the distance between the first coil unit and the second coil unit can be adjusted by pivoting the first leg portion and the second leg portion relative to each other about the hinge portion, wherein the locking element of the bracket structure is configured to mechanically prevent the hinge portion from pivoting the first leg portion and the second leg portion relative to each other.

5. The stimulation device of claim 1, wherein the bracket structure is configured to adjust a first orientation of the first coil unit to a first target orientation of the target configuration and a second orientation of the second coil unit to a second target orientation of the target configuration; or, wherein the bracket structure is configured to adjust the first orientation of the first coil unit to the first target orientation of the target configuration and the second orientation of the second coil unit to the second target orientation of the target configuration, and wherein the locking element of the bracket structure is configured to mechanically prevent adjustment of the first orientation and of the second orientation.

6. The stimulation device of claim 5, wherein the bracket structure comprises a first pivoting coupler and a second pivoting coupler, and wherein the first coil unit is mounted to the first pivoting coupler and the second coil unit is mounted to the second pivoting coupler; or, wherein the bracket structure comprises the first pivoting coupler and the second pivoting coupler, and wherein the first coil unit is mounted to the first pivoting coupler and the second coil unit is mounted to the second pivoting coupler, wherein the first pivoting coupler is configured to provide pivoting the first coil unit relative to the bracket structure about two essentially perpendicular axes and the second pivoting coupler is configured to provide pivoting the second coil unit relative to the bracket unit about two essentially perpendicular axes, wherein the locking element of the bracket structure is configured to mechanically prevent the first pivoting coupler from pivoting the first coil unit and the second pivoting coupler from pivoting the second coil unit.

7. The stimulation device of claim 1, wherein the bracket structure comprises a first frame portion, a second frame portion and a forehead support structure, the first coil unit is coupled to the first frame portion and the second coil unit is coupled to the second frame portion, the first frame portion and the second frame portion are connected via the forehead support structure, and the forehead support structure is configured to be positioned at and to contact a forehead of the human or the animal body.

8. The stimulation device of claim 7, wherein the bracket structure comprises an overhead arch having a first tangential end and a second tangential end, the first frame portion is mounted to the first tangential end of the overhead arch, and the second frame portion is mounted to the second tangential end of the overhead arch; or wherein the bracket structure comprises the overhead arch having the first tangential end and the second tangential end, the first frame portion being mounted to the first tangential end of the overhead arch, and the second frame portion being mounted to the second tangential end of the overhead arch, and wherein the bracket structure is configured such that a distance between the overhead arch and the first coil unit and a distance between the overhead arch and the second coil unit are adjustable.

9. The stimulation device of claim 7, wherein the forehead support structure of the bracket structure is configured to be adjusted in accordance with a size of the forehead of the human or the animal body, and/or wherein the forehead support structure of the bracket structure comprises a band configured to extend along the forehead of the human or the animal body, and/or wherein the forehead support structure of the bracket structure comprises a pad configured to contact the forehead of the human or the animal body, and/or wherein each of the first frame portion and the second frame portion comprise a neck position guide section to which the first coil unit and the second coil unit, respectively, is movably mounted such that the first coil unit and the second coil unit can be varyingly positioned about a neck of the human or the animal body.

10. The stimulation device of claim 9, wherein the locking element of the bracket structure comprises a first fastening member coupled to the first coil unit and configured to be in a fixed state, in which the first coil unit is immovably fastened, and in a loose state, in which the first coil unit is movable, and a second fastening member coupled to the second coil unit and configured to be in a fixed state, in which the second coil unit is immovably fastened, and in a loose state, in which the second coil unit is movable; and the first coil unit is mounted to the neck position guide section of the first frame portion by the first fastening member of the locking element, wherein in the fixed state the first coil unit is immovably fastened to the neck position guide section of the first frame portion and in the loose state the first coil unit is movable relative to the neck position guide section of the first frame portion, and the second coil unit is mounted to the neck position guide section of the second frame portion by the second fastening member of the locking element, wherein in the fixed state the second coil unit is immovably fastened to the neck position guide section of the second frame portion and in the loose state the second coil unit is movable relative to the neck position guide section of the second frame portion.

11. The stimulation device of claim 7, wherein the bracket structure comprises two support structures configured to support the stimulation device on a torso of the human or the animal body, or one of the two support structures is comprised by the first frame portion and the other of the two support structures is comprised by the second frame portion, and/or one of the two support structures comprises a first support bar movably connected to the first frame portion and the other of the two support structures comprises a second support bar movably connected to the second frame portion.

12. The stimulation device of claim 1, wherein the locking element of the bracket structure comprises a first fastening member coupled to the first coil unit and configured to be in a fixed state, in which the first coil unit is immovably fastened, and in a loose state, in which the first coil unit is movable, and a second fastening member coupled to the second coil unit and configured to be in a fixed state, in which the second coil unit is immovably fastened, and in a loose state, in which the second coil unit is movable.

13. The stimulation device of claim 1, comprising a reference structure configured to repeatedly locating the stimulation device at a target position of the human or the animal body.

14. The stimulation device of claim 13, wherein the reference structure comprises at least two through-holes provided in the bracket structure and designed to allow providing markers to the human or the animal body there through.

15. The stimulation device of claim 13, wherein the reference structure comprises at least two connector members configured to be connected to respective connector members applied to the human or the animal body.

16. The stimulation device of claim 1, wherein the bracket structure comprises a vacuum fastener configured to attach the stimulation device to the human or the animal body.

17. The stimulation device of claim 1, wherein the first coil unit has a first forward face configured to be positioned at the human or the animal body, the second coil unit has a second forward face configured to be positioned at the human or the animal body, the bracket structure has a third forward face configured to be positioned at the human or the animal body, and the stimulation device is configured to be arranged at a defined location of the human or the animal body by the first forward face, the second forward face and the third forward face being positioned at the human or the animal body.

18. A method of stimulating two separate Phrenic nerves in a human or animal body for activating a diaphragm in the human or the animal body, comprising:

obtaining a stimulation device according to claim 1;

adjusting a bracket structure of the stimulation device such that positions and orientations of a first coil unit of the stimulation device and of a second coil unit of the stimulation device relative to each other are adapted to the target configuration in which the first coil unit and the second coil unit are distinctly positioned at a neck of the human or the animal body such that a first Phrenic nerve of the human or the animal body can be stimulated by the first coil unit and a second Phrenic nerve of the human or the animal body can be stimulated by the second coil unit; and locking the bracket structure to block the position and orientation of the first coil unit and the second coil unit relative to each other in the target configuration.

19. The method of claim 18, comprising a step of obtaining an activation biofeedback indicative for an activation of the diaphragm induced by the stimulation of the two Phrenic nerves, wherein adjusting the bracket structure comprises varying the positions and orientations of the first and second coil units of the stimulation device and stopping variation of the first and second coil units of the stimulation device when the activation biofeedback is satisfying; or a step of obtaining the activation biofeedback indicative for the activation of the diaphragm induced by the stimulation of the two Phrenic nerves, wherein the adjusting of the bracket structure comprises varying the positions and orientations of the first and second coil units of the stimulation device and stopping variation of the first and second coil units of the stimulation device when the activation biofeedback is satisfying, and a step of arranging a biofeedback sensor to sense for an activation of the target tissue, wherein the activation biofeedback is obtained by provision of a sensor signal generated by the biofeedback sensor.

20. The method of claim 19, further comprising:

gathering the activation biofeedbacks of the varied positions and orientations of the first and second coil units of the stimulation device when varying the positions and orientations of the first and second coil units of the stimulation device, comparing the gathered activation biofeedbacks of the varied positions and orientations of the first and second coil units of the stimulation device to each other, and selecting the position and orientation of the first and second coil units of the stimulation device that maximizes an activation biofeedback as the position and orientation of the first and second coil units of the stimulation device with the satisfying activation biofeedback.

* * * * *